(12) United States Patent
Bergeron, Jr.

(10) Patent No.: US 6,235,794 B1
(45) Date of Patent: *May 22, 2001

(54) BIOLOGICALLY ACTIVE SPERMIDINE ANALOGUES, PHARMACEUTICAL COMPOSITIONS AND METHODS OF TREATMENT

(75) Inventor: Raymond J. Bergeron, Jr., Gainesville, FL (US)

(73) Assignee: University of Florida, Gainesville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/834,807

(22) Filed: Apr. 3, 1997

(51) Int. Cl.[7] .......................... A61K 31/13; C07C 211/00

(52) U.S. Cl. ............................................. 514/674; 564/512

(58) Field of Search ............................. 564/512; 514/674

(56) References Cited

U.S. PATENT DOCUMENTS 4,591,605 * 5/1986 Ray ...................................... 514/674

FOREIGN PATENT DOCUMENTS 0 162 413 * 11/1985 (EP) .

* cited by examiner

*Primary Examiner*—Deborah C. Lambkin
(74) *Attorney, Agent, or Firm*—Miles & Stockbridge; Dennis P. Clarke

(57) ABSTRACT

Polyamines having the formula:

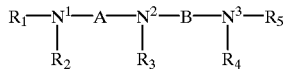

or a salt thereof with a pharmaceutically acceptable acid wherein: $R_1$–$R_5$ may be the same or different and are alkyl, aryl, aryl alkyl, cycloalkyl or hydrogen; at least one of $R_1$ and $R_2$ and at least one of $R_4$ and $R_5$ are not hydrogen, and any of the alkyl chains may optionally be interrupted by at least one etheric oxygen atom, excluding $N^1,N^3$-diethylspermidine and $N^1,N^3$-dipropylspermidine; and A and B are bridging groups which effectively maintain the distance between the nitrogen atoms such that the polyamine: (i) is capable of uptake by a target cell upon administration of the polyamine to a human or non-human animal; and (ii) upon uptake by the target cell, competitively binds via an electrostatic interaction between the positively charged nitrogen atoms to substantially the same biological counter-anions as the intracellular natural polyamines in the target cell.

35 Claims, 7 Drawing Sheets

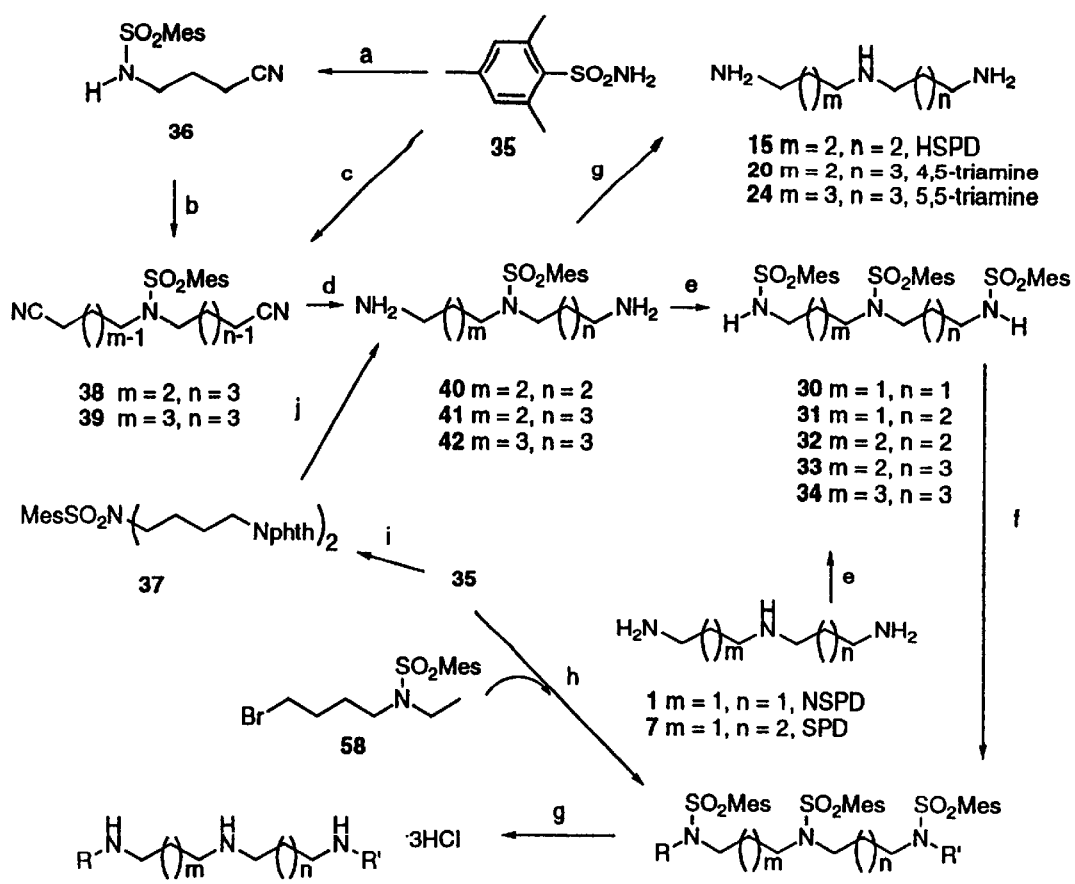

Reagents (a) 4-bromobutyronitrile/NaH/DMF; (b) 5-bromovaleronitrile/NaH/DMF; (c) NaH/DMF/4-bromobutyronitrile or 5-chlorovaleronitrile; (d) $H_2$/Ra Ni/$NH_3$/$CH_3OH$; (e) mesitylenesulfonyl chloride/NaOH(aq)/$CH_2Cl_2$; (f) NaH/DMF/haloalkane; (g) 30% HBr in HOAc/PhOH/$CH_2Cl_2$, HCl. (h) NaH/DMF; (i) N-(4-bromobutyl)phthalimide/NaH/DMF; (j) $(H_2N)_2 \cdot H_2O$/EtOH.

Scheme 1. Synthesis of analogues of NSPD, SPD, HSPD, 4,5- and 5,5-triamines.

FIG. 1

Reagents: (a) NaH/DMF; (b) NaH/DMF/1,5-dibromopentane; (c) TFA/CH$_2$Cl$_2$; (d) 30% HBr/HOAc/PhOH, HCl. Scheme 2. Synthesis of DE(4,5) (22).

Reagents: (a) mesitylenesulfonyl chloride/1 N NaOH(aq)/CH$_2$Cl$_2$; (b) NaH /DMF/
1,3-dibromopropane (m = 1) or 1,4-dibromobutane (m = 2); (c) Ph$_3$CCl/CH$_2$Cl$_2$;
(d) NaH/DMF/66 or 67; (e) 30% HBr in HOAc/PhOH/CH$_2$Cl$_2$, HCl.

Scheme 3. Synthesis of monopropyl SPD and HSPD analogues.

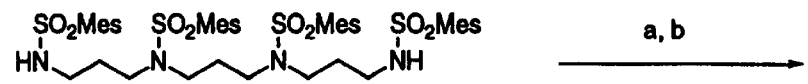
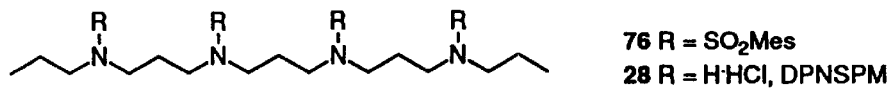
Reagents: (a) NaH/DMF/n-PrI; (b) 30% HBr in HOAc/PhOH/CH$_2$Cl$_2$, then HCl
Scheme 4. Synthesis of DPNSPM (28).
FIG. 4
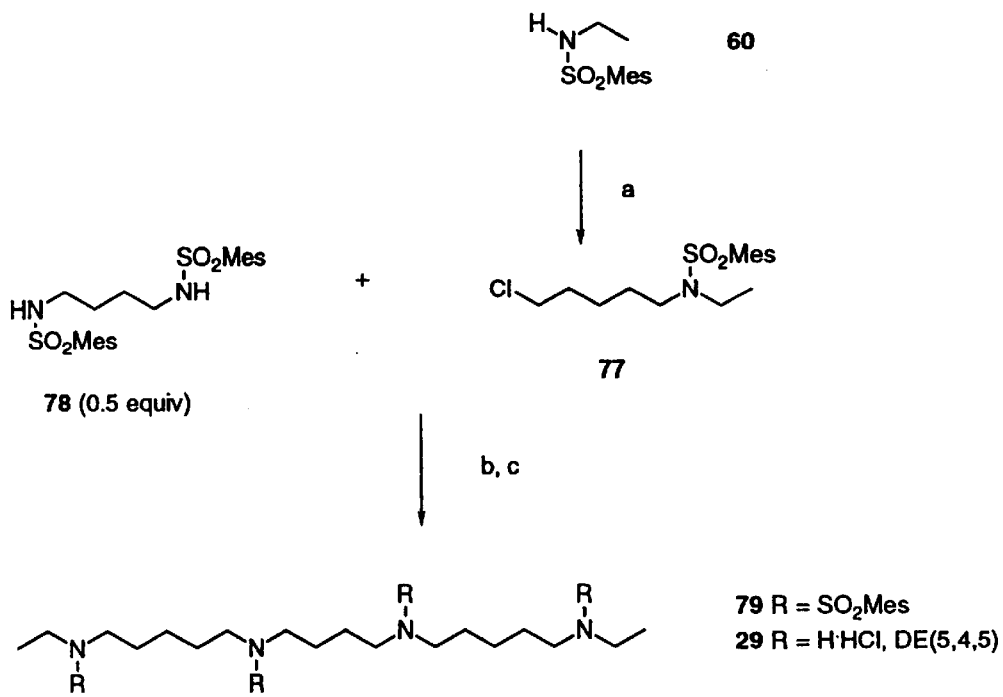
Reagents: (a) NaH/DMF/excess 1,5-dichloropropane; (b) NaH/DMF; (c) 30% HBr in HOAc/PhOH/CH$_2$Cl$_2$, then HCl.
Scheme 5. Synthesis of DE(5,4,5) (29).
FIG. 5

The structure-activity relationship between the triamine analogues and SSAT upregulation.

The structure-activity relationship between the tetraamine analogues and SSAT upregulation.

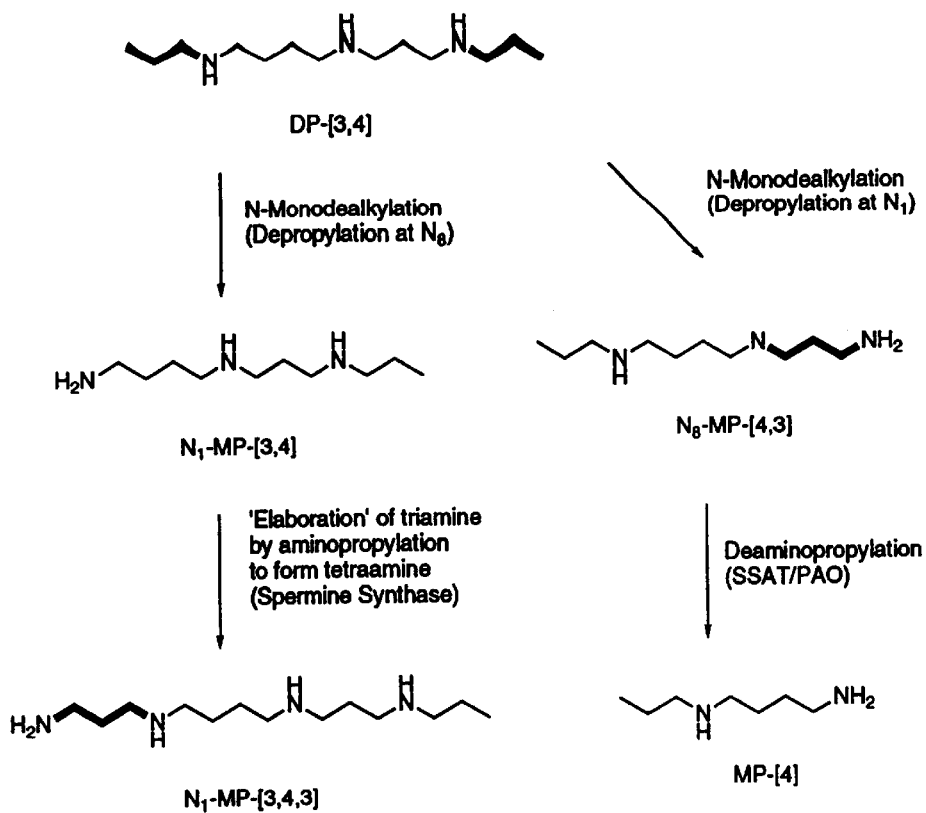

Three Types of Metabolic Transformation of Bisalkyltriamines in L1210 Cells. (a) N-Dealkylation is a prequisite for further metabolism. In L1210 cells: N-depropylation > N-deethylation. No N-demethylation was observed. (b) Deaminopropylation by SSAT/PAO can occur if N-dealkylation exposes a primary aminopropyl terminus. Deaminopropylation is most pronounced in analogues with a norspermine, [3,3,3], or norspermidine, [3,3], backbone. (c) Elaboration of a triamine to the corresponding tetraamine can occur when N-dealkylation exposes a primary aminobutyl terminus which can be aminopropylated by spermine synthase. Only analogues or metabolites with a spermidine, [3,4], backbone appear to serve as substrates (i.e., $N^1$-alkyl-[3,4]; not $N^8$-alkyl-[4,3], N-alkyl-[3,3], N-alkyl-[4,4], or $N^{10}$-alkyl-[5,4]).

FIG. 7

The structure-activity relationship between the triamine analogues and $K_i$ values.

The structure and activity relationship between the polyamine analogues and $IC_{50}$ values. (a) Triamine analogues (b) Tetraamine analogues

BIOLOGICALLY ACTIVE SPERMIDINE ANALOGUES, PHARMACEUTICAL COMPOSITIONS AND METHODS OF TREATMENT

BACKGROUND OF THE INVENTION

1. Field of the Invention

The present invention relates to novel polyamines useful as active ingredients in pharmaceutical compositions and therapeutic methods of treatment.

2. Description of the Prior Art

Because of the sustained increases in polyamine biosynthesis in pre-neoplastic and neoplastic tissues, a great deal of attention has been directed to the polyamine biosynthetic network as a target in anti-neoplastic strategies [Pegg, "Polyamine Metabolism and Its Importance in Neoplastic Growth and as a Target for Chemotherapy," *Cancer Res.*, Vol. 48, pages 759–774 (1988); and Marton et al, "Directions for Polyamine Research," *J. Cell Biochem.*, Vol. 45, pages 7–8 (1991)]. Initial work focused on the design and synthesis of compounds which would inhibit L-ornithine decarboxylase (ODC) [Bey et al, "Inhibition of Basic Amino Acid Decarboxylases Involved in Polyamine Biosynthesis," *Inhibition of Metabolism Biological Significance and Basis for New Therapies*, McCann et al, eds.; Academic Press: Orlando, Fla., pages 1–32 (1987)] and S-adenosyl-L-methionine decarboxylase (AdoMetDC) [Pegg, *Cancer Res.*, Vol. 48, supra; and Williams-Ashman et al, "Methylgly-oxal Bis(guanylhydrazone) as a Potent Inhibitor of Mammalian and Yeast S-Adenosylmethionine Decarboxylases," *Biochem. Biophys. Res. Commun.*, Vol. 46, pages 288–295 (1972)]. Some success was achieved through this approach in that difluoromethylornithine (DFMO), an ODC inhibitor, and methylglyoxylbis (guanylhydrazone) (MGBG), an AdoMetDC inhibitor, were effective against both in vivo and in vitro tumors [Sunkara et al, "Inhibitors of Polyamine Biosynthesis: Cellular and In Vivo Effects on Tumor Proliferation," *Inhibition of Polyamine Metabolism Biological Significant Cause and Basis for New Therapies*, McCann et al, eds.; Academic Press: Orlando, Fla., pages 121–140 (1987); and Pegg et al, "S-Adenosylmethionine Decarboxylase as an Enzyme Target for Therapy," *Pharmacol. Ther.*, Vol. 56, pages 359–377 (1992)]. However, clinical trials did not mirror the success realized in the model systems; the drug either was too toxic as with MGBG [Pegg et al, *Biochem. Pharmacol.*, Vol. 27, pages 1625–1629 (1978)] or was unable to show significant impact on tumors in humans as with DFMO [Schecter et al, "Clinical Aspects of Inhibition of Ornithine Decarboxylase with Emphasis on the Therapeutic Trials of Eflornithine (DFMO) in Cancer and Protozoan Diseases," *Inhibition of Polyamine Metabolism. Biological Significance and Basis for New Therapies*, McCann et al, eds.; Academic Press: Orlando, Fla., pages 345–364 (1987)]. One of the problems with the target enzymes ODC and AdoMetDC is associated [Seiler et al, "Polyamine Transport in Mammalian Cells," *Int. J. Biochem.*, Vol. 22, pages 211–218 (1990)] with their very short half-lives, i.e., about 20 minutes. This can translate into a protracted exposure requirement for patients which is a less than desirable situation. Nonetheless, both DFMO and MGBG served well as proof of principle that the polyamine biosynthetic network was an excellent target in the design of anti-cancer drugs.

It would thus be desirable to design polyamine analogues which would be incorporated via the polyamine transport apparatus and, once in the cell, would find their way to the same subcellular distribution sites as the normal polyamines do, but would be unable to be further processed [Jänne et al, "Polyamines in Rapid Growth and Cancer," *Biochim. Biophys. Acta*, Vol. 473, page 241 (1978); and Porter et al, "Enzyme Regulation as an Approach to Interference with Polyamine Biosynthesis—an Alternative to Enzyme Inhibition," *Enzyme Regul.*, Vol. 27, pages 57–79 (1988)]. They would appear enough like the natural polyamines to shut down polyamine enzymes just as when the cells are exposed to exogenous spermine.

Thus, a series of terminally N-alkylated tetraamines, which exhibit anti-neoplastic activity against a number of murine and human tumor lines both in vitro and in vivo, were assembled [Bergeron et al, "Synthetic polyamine analogues as antineoplastics," *J. Med. Chem.*, Vol. 31, pages 1183–1190 (1988); Bergeron et al, "Antiproliferative Properties of Polyamine Analogues: a Structure-Activity Study," *J. Med. Chem.*, Vol. 37, pages 3464–3476 (1994); Bernacki et al, "Antitumor Activity of N,N'-Bis(ethyl)spermine Homologues Against Human MALME-3 Melanoma Xenografts," *Cancer Res.*, Vol. 52, pages 2424–2430 (1992); Porter et al, "Biological Properties of $N^4$-Spermidine Derivatives and Their Potential in Anti-cancer Chemotherapy," *Cancer Res.*, Vol. 42, pages 4072–4078 (1982); and Porter et al, "Biological Properties of $N^4$- and $N^1,N^8$-Spermidine Derivatives in Cultured L1210 Leukemia Cells," *Cancer Res.*, Vol. 45, pages 2050–2057 (1985)]. These tetraamines have been shown to utilize the polyamine transport apparatus for incorporation [Bergeron et al,*J. Med. Chem.*, Vol. 37, supra; and Porter et al, "Aliphatic Chain Length Specific of the Polyamine Transport System in Ascites L1210 Leukemia Cells," *Cancer Res.*, Vol. 44, pages 126–128 (1984)], deplete polyamine pools [Bergeron et al, "Role of the Methylene Backbone in the Antiproliferative Activity of Polyamine Analogues on L1210 Cells," *Cancer Res.*, Vol. 49, pages 2959–2964 (1989)], drastically reduce the level of ODC [Pegg et al, "Control of Ornithine Decarboxylase Activity in α-Difluoromethylornithine-Resistant L1210 Cells by Polyamines and Synthetic Analogues," *J. Biol. Chem.*, Vol. 263, pages 11008–11014 (1988); and Porter et al, "Relative Abilities of Bis(ethyl) Derivatives of Putrescine, Spermidine and Spermine to Regulate Polyamines Biosynthesis and Inhibit L1210 Leukemia Cell Growth," *Cancer Res.*, Vol. 47, pages 2821–2825 (1987)] and AdoMetDC activities [Pegg et al, *J. Biol. Chem.*, Vol. 263, supra; and Porter et al, *Cancer Res.*, Vol. 47, supra] and in some cases to up-regulate spermidine/spermine/$N^1$-acetyltransferase (SSAT) [Pegg et al, "Effect of $N^1,N^{12}$-Bis (ethyl)spermine and Related Compounds on Growth and Polyamine Acetylation, Content and Excretion in Human Colon Tumor Cell," *J. Biol. Chem.*, Vol. 264, pages 11744–11749 (1989); Casero et al, "Differential Induction of Spermidine/Spermine $N^1$-Acetyltransferase in Human Lung Cancer Cells by the Bis(ethyl)polyamine Analogues," *Cancer Res.*, Vol. 49, pages 3829–3833 (1989); Libby et al, "Major Increases in Spermidine/Spermine-$N^1$-

Acetyltransferase by Spermine Analogues and Their Relationship to Polyamine Depletion and Growth Inhibition in L1210 Cells," *Cancer Res.*, Vol. 49, pages 6226–6231 (1989); Libby et al, "Structure-Function Correlations of Polyamine Analog-Induced Increases in Spermidine/Spermine Acetyltransferases Activity," *Biochem. Pharmacol.*, Vol. 38, pages 1435–1442 (1989); Porter et al, "Correlations Between Polyamine Analog-Induced Increases in Spermidine/Spermine N-Acetyltransferase Activity, Polyamine Pool Depletion and Growth Inhibition in Human Melanoma Cell Lines," *Cancer Res.*, Vol. 51, pages 3715–3720 (1991); Fogel-Petrovic et al, "Polyamine and Polyamine Analog Regulation of Spermidine/Spermine $N^1$-Acetyltransferase in MALME-3M Human Melanoma Cells," *J. Biol. Chem.*, Vol. 268, pages 19118–19125 (1993); and Shappell et al, "Regulation of Spermidine/Spermine $N^1$-Acetyltransferase by Intra-cellular Polyamine Pools-Evidence for a Functional Role in Polyamine Homeostasis," *FEBS Lett.*, Vol. 321, pages 179–183 (1993)]. Interestingly, on incorporation of the tetraamine analogues, the total picoequivalents of charge associated with the analogues, as well as the natural polyamines, is maintained for about 24 hours. Thus, as the cell is incorporating n picoequivalents of drug, it is excreting n picoequivalents of natural polyamines.

Very small structural alterations in these spermine analogues and homologues result in substantial differences in their biological activity [Bergeron et al, *Cancer Res.*, Vol. 49, supra]. For example, while the tetraamines $N^1,N^{12}$-diethyl-spermine (DESPM), $N^1,N^{11}$-diethylnorspermine (DENSPM) and $N^1,N^{14}$-diethylhomospermine (DEHSPM) suppress ODC and AdoMetDC to about the same level at equimolar concentrations, the effect of both DESPM and DEHSPM on cell growth occurs earlier than that observed for DENSPM. The $K_i$ value of DENSPM is over 10 times as great [Bergeron et al, *Cancer Res.*, Vol. 49, supra] as those of DESPM and DEHSPM for the polyamine transport system. However, the most notable difference between the three analogues is related to their ability to stimulate SSAT [Casero et al, *Cancer Res.*, Vol. 49, supra; Libby et al, *Cancer Res.*, Vol. 49, supra; Libby et al, *Biochem. Pharmacol.*, Vol. 38, supra; and Porter et al, *Cancer Res.*, Vol. 51, supra]. The tetraamine DENSPM up-regulates SSAT by 1200 fold in MALME-3 cells, while DESPM and DEHSPM stimulate SSAT by 250- and 30-fold, respectively [Porter et al, *Cancer Res.*, Vol. 51, supra]. Thus, the impact of the tetraamine compounds on cell growth was shown to be dependent on: the distance between the nitrogens; the nature of the terminal alkyl substituents [Bergeron et al, *J. Med. Chem.*, Vol. 37, supra] and, most importantly, on the charge status of the molecules [Bergeron et al, "The Role of Charge in Polyamine Analogue Recognition," *J. Med. Chem.*, Vol. 38, pages 2278–2285 (1995)].

It was decided to establish whether or not a similar structure activity relationship exists for triamines, i.e., analogues of spermidine. The importance of this issue is underscored by the tremendous difference in toxicity between the triamines and tetraamines in general. Triamines are much less toxic, thus making them of potentially useful therapeutic value [Bergeron et al, "Metabolism and Pharmacokinetics of $N^1,N^{11}$-Diethylnorspermine," *Drug Metab. Dispos.*, Vol. 23, pages 1117–1125 (1995)].

It is, therefore, an object of the present invention to provide certain novel triamines possessing biological activity, in particular, anti-neoplastic activity.

SUMMARY OF THE INVENTION

This and other objects are realized by the present invention, one embodiment of which relates to polyamines not occurring in nature having the formula:

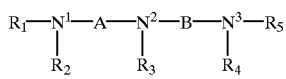

or a salt thereof with a pharmaceutically acceptable acid wherein:

$R_1$–$R_5$ may be the same or different and are alkyl, aryl, aryl alkyl, cycloalkyl or hydrogen; at least one of $R_1$ and $R_2$ and at least one of $R_4$ and $R_5$ are not hydrogen, and any of the alkyl chains may optionally be interrupted by at least one etheric oxygen atom, excluding $N^1,N^3$-diethylspermidine and $N^1,N^3$-dipropylspermidine; and A and B may be the same or different and are bridging groups including unsubstituted heterocyclic bridging groups which effectively maintain the distance between the nitrogen atoms such that the polyamine: (i) is capable of uptake by a target cell upon administration of the polyamine to a human or non-human animal; and (ii) upon uptake by the target cell, competitively binds via an electrostatic interaction between the positively charged nitrogen atoms to substantially the same biological counter-anions as the intra-cellular natural polyamines in the target cell, provided that where A or B is a heterocyclic bridging group, the bridging group is an unsubstituted heterocyclic group incorporating said $N^1$, $N^2$ or $N^3$ atoms in the heterocyclic ring as an unsubstituted N atom; the polyamine, upon binding to the biological counter-anion in the cell, functions in a manner biologically different than the intracellular polyamines.

A further embodiment of the invention concerns a pharmaceutical composition in unit dosage form comprising a pharmaceutically acceptable carrier and a pharmaceutically effective amount of a polyamine as described above or a salt thereof with a pharmaceutically acceptable acid.

An additional embodiment of the invention comprises a method of treating a human or non-human patient in need thereof comprising administering thereto a pharmaceutically effective amount of a polyamine described above or a salt thereof with a pharmaceutically acceptable acid.

Other embodiments of the invention will become apparent from the following detailed description of the invention.

BRIEF DESCRIPTION OF THE DRAWINGS

FIGS. 1–5 depict reaction schemes for the syntheses of the polyamines of the invention.

FIG. 7 elaborates the metabolic transformation of the triamine analogues.

DETAILED DESCRIPTION OF THE INVENTION

Figure 2:
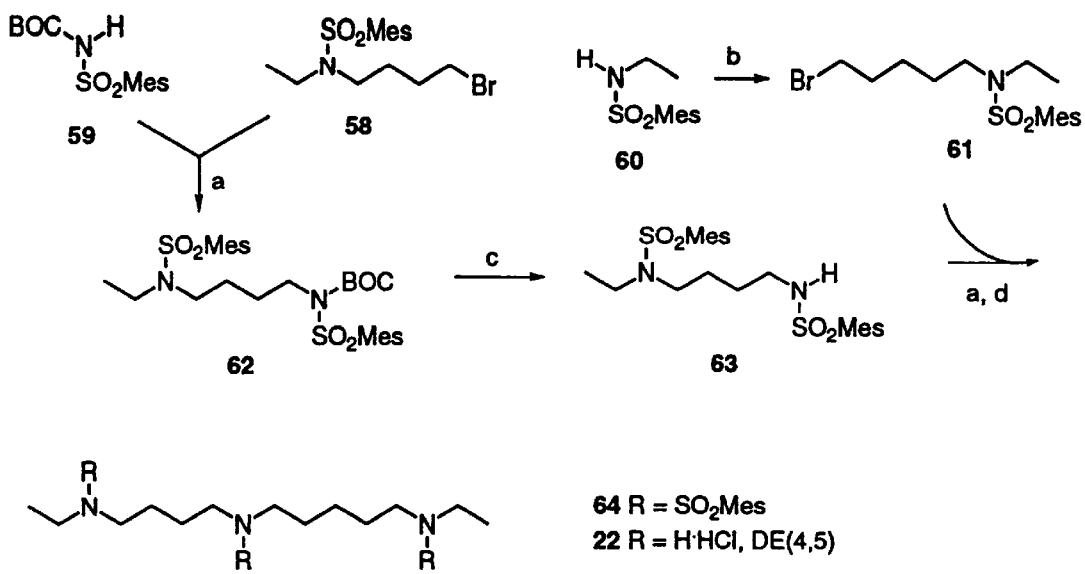

In the polyamines of the invention, as described in the above structural formula, $R_1$–$R_6$ may be alkyl, e.g., methyl, ethyl, n-propyl, isopropyl, n-butyl, isobutyl, sec-butyl, tert-butyl; aryl, e.g., phenyl, p-tolyl, 2,4,6-trimethylphenyl; aryl alkyl, e.g., benzyl, α-phenethyl, β-phenethyl; cycloalkyl, e.g., cyclohexyl, cyclobutyl, cyclopentyl, cycloheptyl; any of the foregoing wherein the alkyl chain is interrupted by etheric oxygen, e.g., $CH_3O(CH_2)_2$—, $CH_3O(CH_2)_2O(CH_2)_2$—, $CH_3O(CH_2)_2O(CH_2)_2O(CH_2)_2$—; or hydrogen.

Except where $R_1$–$R_6$ are hydrogen or etheric substituents, each are hydrocarbyl and may have from about 1 to about 10 carbon atoms, it being understood that the size of the substituents will be tailored in each case to ensure that the polyamine is capable of uptake by the target cell and, upon uptake, will competitively bind with the intracellular counter-anions as described above.

The bridging groups A and B may be the same or different and may be alkylene having 1–8 carbon atoms, e.g., methylene, trimethylene, tetramethylene, pentamethylene; branched alkylene, e.g., —CH(CH₃)CH₂CH₂-, —CH₂CH(CH₃)CH₂—, —CH(CH₃)CH₂CH₂—, —CH₂CH(CH₃)CH₂CH₂—; arylalkylene, e.g., —CH(Ph)CH₂CH₂—, —CH₂CH(Ph)CH₂—, —CH(Ph)CH₂CH₂CH₂—, —CH₂CH(Ph)CH₂—CH₂—; cycloalkylene, e.g., cyclohexylene, cis- and trans-1,3-cyclohexylene, 1,4-cyclohexylene, 1,3-cyclopentylene; heterocyclic groups which incorporate within the ring one of the nitrogen atoms of the polyamine [e.g.,

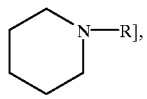

it being understood that the heterocyclic nitrogen group may be located at the terminal end(s) or within the interior of the polyamine.

Those skilled in the art will appreciate that it is only necessary that the bridging groups be selected so as to ensure uptake by the cell and competitive binding to the intracellular counter-anion as described above.

At physiological pH's, the naturally occurring polyamines and the analogs of the present invention are largely in a protonated state [Bergeron et al, "Hexahydropyrimidines as masked spermidine vectors in drug delivery," *Bioorg. Chem.*, Vol. 14, pages 345–355 (1986)]. At a cellular level, these polycations can bind to a collection of single unconnected anions or to anions tethered to a single biomolecule, e.g., the phosphates on a nucleic acid.

If there is any significance to the role of charge interaction in the biological properties of the polyamine analogs, alterations in the polyamine methylene backbone should have significant impact on the compound's biological properties.

In fact, the significance of charge and the length of the methylene bridges separating the cations in the biological properties of the polyamine analogs has been demonstrated.

Among the most preferred polyamines of the invention are those of the following formula:

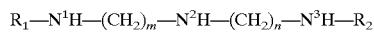

wherein: $R_1$ and $R_2$ may be the same or different and are H or alkyl; preferably having, at most, 10 carbon atoms; most preferably, methyl, ethyl and n-propyl (with the proviso that both $R_1$ and $R_2$ may not be H); and m and n may be the same or different and are 3, 4 or 5.

Exemplary of preferred polyamines of the invention are:
dimethylnorspermidine (DMNSPD)
monoethylnorspermidine (MENSPD)
diethylnorspermidine (DENSPD)
monopropylnorspermidine (MPNSPD)
dipropylnorspermidine (DPNSPD)
dimethylspermidine (DMSPD)
monoethylspermidine [(MESPD)N1]
monoethylspermidine [(MESPD)N8]
diethylspermidine (DESPD)
monopropylspermidine [(MPSPD)N1]
monopropylspermidine [(MPSPD)N8]
dipropylspermidine (DPSPD)
dimethylhomospermidine (DMHSPD)
diethylhomospermidine (DEHSPD)
monopropylhomospermidine (MPHSPD)
dipropylhomospermidine (DPHSPD)
$CH_3NH(CH_2)_4NH(CH_2)_5NHCH_3$ [DM(4,5)]
$CH_3CH_2NH(CH_2)_4NH(CH_2)_5NHCH_2CH_3$ [DE(4,5)]
$CH_3(CH_2)_2NH(CH_2)_4NH(CH_2)_5NH(CH_2)_2CH_3$ [DP(4,5)]
$CH_3NH(CH_2)_5NH(CH_2)_5NHCH_3$ [DM(5,5)]
$CH_3CH_2NH(CH_2)_5NH(CH_2)_5NHCH_2CH_3$ [DE(5,5)]
$CH_3(CH_2)_2NH(CH_2)_5NH(CH_2)_5NH(CH_2)_2CH_3$ [DP(5,5)]

It will be understood by those skilled in the art that the polyamines of the present invention may be employed to effect any desired biological effect mediated by the polyamine biosynthetic network or system, e.g., anti-neoplastic, anti-viral, anti-psoriasis, anti-inflammatory, anti-arrhythmic, etc.

For the purposes of a detailed description of a preferred embodiment of the invention, however, the activity of a representative number of polyamines against tumor cells sensitive thereto will be described.

The triamines of the invention described hereinbelow can be envisioned as belonging to one of two families of polyamines having the structural formula:

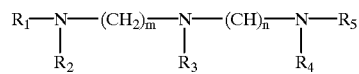

One family of polyamines can be characterized as having symmetrical methylene backbones, i.e., wherein m=n.

The other family is unsymmetrical, i.e., m≠n.

Synthesis of Triamines. The two families of triamines were synthesized: (1) those with symmetrical methylene backbones, i.e., derived from the parent polyamines norspermidine (3,3), homospermidine (4,4) or the longer triamine (5,5) [wherein (3,3), (4,4) and (5,5) refer to the number of methylene groups, i.e., (m,n)], with an alkyl group at one or both terminal nitrogens; and (2) those with unsymmetrical methylene backbones, i.e., from the parent polyamines spermidine (3,4) or the (4,5) triamine, with an alkyl group at one or both terminal nitrogens (Table 1). The numbers in parentheses refer to the number of methylenes separating successive nitrogens. In the case of the $N^\alpha,N^\omega$-disubstituted norspermidine (m=3, n=3) and spermidine (m=3, n=4) analogues, the commercially available triamines norspermidine (NSPD) (1) and spermidine (SPD) (7) were reacted with mesitylenesulfonyl chloride (3 equiv) under biphasic conditions ($CH_2Cl_2$/dilute NaOH) to give 30 [Bergeron et al, *Drug Metab. Dispos.*, Vol. 23, supra], and 31, respectively (step e) (FIG. 1, Scheme 1). These trisulfonamides were deprotonated with NaH in DMF and treated with an excess of the appropriate primary alkyl iodide to make intermediates 43, 44 and 46–49 (step f). Finally, the mesitylenesulfonyl blocking groups were cleanly removed under reductive conditions utilizing 30% HBr in HOAc and phenol in $CH_2Cl_2$ (step g) to give terminal dimethyl-(2, 8), diethyl-(4, 11), and dipropyl-(6, 14) NSPD and SPD, respectively, which were isolated as their recrystallized trihydrochloride salts.

The symmetrical triamines homospermidine (HSPD) (15) (4,4) and 1,7,13-triazatridecane (24) (5,5), which were not commercially available, and their terminally dialkylated derivatives were synthesized by a segmented synthesis (FIG. 1, Scheme 1). Mesitylenesulfonamide (35) [Bergeron et al, *Drug Metab. Dispos.*, Vol. 23, supra] was dialkylated with either N-(4-bromobutyl)phthalimide to give 37 (step i) or with 5-chlorovaleronitrile to furnish 39 (step c). Hydrogenation of the cyano groups of 39 with Raney nickel in methanolic ammonia gave N,N-bis(5-aminopentyl) mesitylenesulfonamide (42) (step d), which provided 5,5-triamine 24 in good yield by treatment with 30% HBr in HOAc (step g). Use of the aromatic imide blocking group in 37 avoided the solubility problems during attempted hydrogenation (Raney nickel, methanolic $NH_3$) of N,N-bis(3-cyanopropyl)mesitylenesulfonamide. Hydrazinolysis of 37 in refluxing EtOH (step j) led to N,N-bis(4-aminobutyl) mesitylenesulfonamide (40). HSPD (15) itself resulted from reductive deprotection of monosulfonamide 40 (step g). Terminal diamines 40 and 42 were converted to their mesitylenesulfonamides 32 and 34, respectively, (step e) and were alkylated with the appropriate primary halide (step f). Hydrogen bromide-promoted deprotection of masked analogues 50, 52 and 55–57 yielded DMHSPD (16), DPHSPD (19), DM(5,5) (25), DE(5,5) (26) and DP(5,5) (27), respectively.

$N^1,N^9$-Diethylhomospermidine (DEHSPD) (17) was made by a convergent route (FIG. 1, Scheme 1). Alkylation of sulfonamide 35 with N-(4-bromobutyl)-N-ethylmesitylenesulfonamide (58) (Bergeron et al, *J. Med. Chem.*, Vol. 37, supra] (2 equiv) led to triprotected analogue 51 (step h), which was unmasked with HBr/HOAc, giving DEHSPD (17) (step g).

3,8,14-Triazahexadecane [DE(4,5)] (22), the terminally diethylated analogue of the unsymmetrical 4,5-triamine, was assembled from N-(tert-butoxycarbonyl)-N-mesitylenesulfonamide (59), a diprotected ammonia synthon [Bergeron et al, *J. Med. Chem.*, Vol. 37, supra] (FIG. 2, Scheme 2). Alkylation of reagent 59 with N-(4-bromobutyl)-N-ethylsulfon-amide (58) (NaH/DMF) (step a) gave triprotected monoethylputrescine 62. The BOC group of 62 was removed with trifluoroacetic acid (TFA) (step c). The resulting sulfonamide 63 was alkylated with N-(5-bromopentyl)-N-ethylmesitylenesulfonamide (61) (step a), which was made from ethylsulfonamide 60 and excess 1,5-dibromopentane (NaH/DMF) (step b), to generate fully protected triamine 64. Deprotection of the amino groups of 64 with HBr led to the diethylated analogue 22 (step d).

The 4,5-triamine 1,6,12-triazadodecane (20) and its dialkylated analogues 2,7,13-triazatetradecane [DM(4,5)] (21) and 4,9,15-triazaoctadecane [DP(4,5)] (23) were produced by a segmented synthesis (FIG. 1, Scheme 1). Consecutive mono-alkylation of sulfonamide 35 with 4-bromobutyronitrile (step a) and 5-bromovaleronitrile (step b) generated dinitrile 38. The cyano groups of 38 were reduced in a Parr shaker with Raney nickel in methanolic ammonia (step d), resulting in primary amine 41. Cleavage of the sulfonyl group of 41 with HBr (step g) produced the parent 4,5-triamine 20. Treatment of 41 with mesitylenesulfonyl chloride (2 equiv) gave 33 (step e), which was terminally dialkylated with iodomethane to 53 or with 1-iodopropane to 54 (step f). Unmasking the amino groups led to dimethylated and dipropylated 4,5-analogues 21 and 23, respectively (step g).

Figure 3:
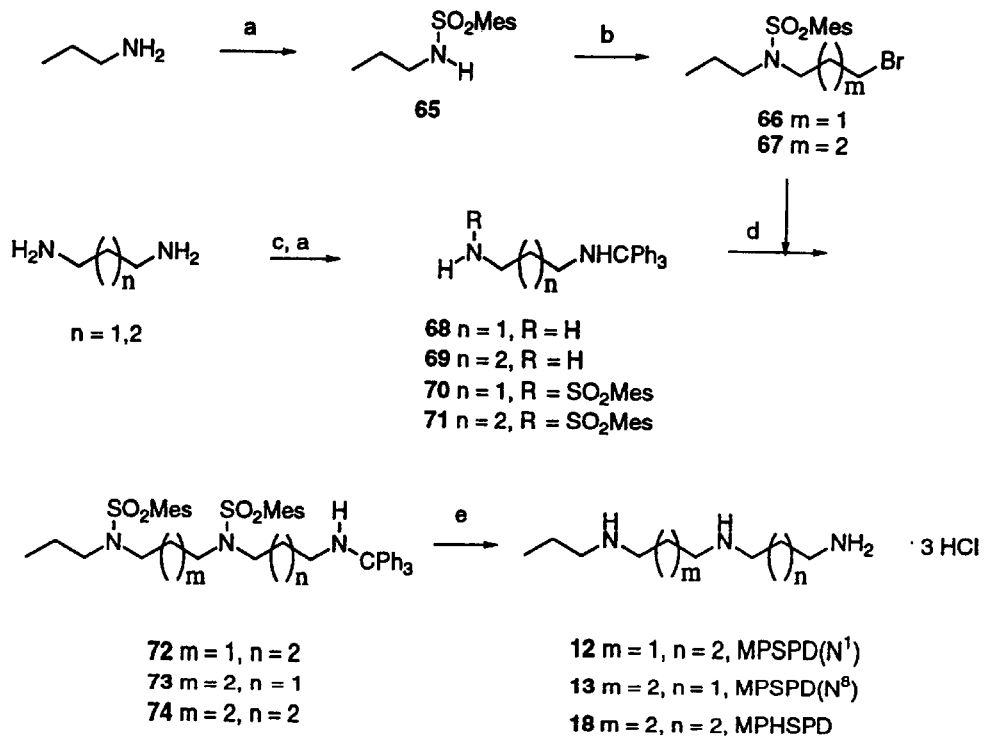

$N^1$-Propylnorspermidine (MPNSPD) (5) was made by treating trimesitylenesulfonyl NSPD 30 [Bergeron et al, *Drug Metab. Dispos.*, Vol. 23, supra] with 1-iodopropane (1 equiv/NaH/DMF), and isolating 45 from the statistical mixture of mono- and di-alkylated products by flash column chromatography (step f) (FIG. 1, Scheme 1). Since SPD is unsymmetrical, reaction of its trisulfonamide 31 with a primary alkyl iodide (1 equiv) would lead to $N^1$- and $N^8$-monoalkylated products, which may be difficult to separate. Thus, the synthesis of both SPD and the HSPD monopropyl analogues required a fragment synthesis (FIG. 3, Scheme 3). N-Propylmesitylenesulfonamide (65) was converted to 3-bromopropyl 66 or 4-bromobutyl reagent 67, with the required dibromoalkane in excess (NaH/DMF). Triphenylmethyl chloride was stirred at room temperature with either 1,3-diaminopropane or 1,4-diaminobutane (5 equiv) in $CH_2Cl_2$ (step c), resulting in $N^1$-tritylated-trimethylenediamine 68 or -putrescine 69. Sulfonation of 68 and 69 occurred at the primary nitrogen and not next to the bulky triphenylmethyl group to give N,N'-disubstituted diamines 70 and 71, respectively (step a). Reaction of the anions of 70 or 71 with the appropriate bromide 66 or 67 resulted in regiospecific N-alkylation at the sulfonamide terminus. Specifically, reaction of 70 with 67 gave 73, and 71 plus 66 or 67 led to 72 or 74, respectively. The protecting groups of 45 and 72–74 were removed simultaneously with Hbr in HOAc/PhOH, resulting in MPNSPD (5), MPSPD ($N^1$) (12), MPSPD($N^8$) (13) and MPHSPD (18), respectively.

Both $N^1$-(9) and $N^8$-ethylspermidine (10) were obtained from reduction of the requisite monoacetylspermidine with lithium aluminum hydride in hot THF, thus completing the synthesis of the triamine series.

Tetraamine analogue $N^1,N^{11}$-dipropylnorspermine (DPNSPM) (28) was accessed from commercially available norspermine (FIG. 4, Scheme 4). Bis-alkylation of the tetrasulfonamide dianion of 75 [Bergeron et al, *J. Med. Chem.*, Vol. 37, supra] with 1-iodopropane (step a) and facile removal of the mesitylenesulfonyl blocking groups of 76 with HBr (step b) generated DPNSPM (28).

The longer polyamine 3,9,14,20-tetraazadocosane [DE(5, 4,5)] (29), the terminally diethylated derivative of the unknown (5,4,5) tetraamine, was synthesized in three high yield steps by the segmenting method (FIG. 5, Scheme 5). N-Ethylmesitylenesulfonamide (60) [Schreinemakers, *Recl. Trav. Chim. Pays-Bas Belg.*, Vol. 16, pages 411–424 (1897)]

was deprotonated (NaH/DMF) and treated with 1,5-dichloropentane (10 equiv), resulting in alkyl chloride 77 (step a). $N^1,N^4$-Bis(mesitylenesulfonyl)putrescine (78) [Bergeron et al, *J. Med. Chem.*, Vol. 37, supra] was alkylated with synthon 77 to give masked tetraamine 79 (step b). The four blocking groups were removed with HBr (step c) to furnish DE(5,4,5) 29 as its crystalline tetrahydrochloride salt.

Biological Evaluations. In summarizing the biological properties of the polyamine analogues, the results are separated into three sets of measurements: the 48- and 96-hour $IC_{50}$ values against L1210 cells and the corresponding $K_i$ values for the polyamine transport apparatus (Table 1); the effect on polyamine pools (Table 2); and the impact on ODC, AdoMetDC and SSAT (Table 3). The compounds are arranged in sets by increasing length, e.g., norspermidine, spermidine, homospermidine, (4,5)- and (5,5)-triamines. Each set is ordered in terms of the size of the terminal alkyl groups. While the $IC_{50}$ and $K_i$ values of DESPD and its impact on polyamine pools, ODC, AdoMetDC and SSAT have been previously reported [Porter et al, *Cancer Res.*, Vol. 45, supra], the measurements on this compound were repeated so that the appropriate positive control and not a historical control would be in place. In order to showcase the importance of the polyamine's overall chain length in structure-activity relationships, there is included a brief commentary of results of tetraamine analogues [Bergeron et al, *J. Med. Chem.*, Vol. 37, supra] where available. Thus, numbers included in parentheses in the tables represent the values for the corresponding tetraamine analogues. A brief discussion is also presented on the metabolic profile of the triamines and on the cationic conservation of charge the cell maintains as defined by the polyamines. Finally, a comparison of the acute and chronic in vivo toxicities of several key triamines and tetraamines is presented.

Antiproliferative Activity—$IC_{50}$ of L1210 cells. As shown in Table 1, NSPD is the most active among the NSPD family of analogues with an $IC_{50}$ of 0.9 $\mu$M at 48 hours and 0.5 $\mu$M at 96 hours. This activity is probably related to the fact that this triamine can easily be converted to toxic metabolites [Alarcon et al, "Evidence for the Formation of Cytotoxic Aldehyde Acrolein from Enzymatically Oxidized Spermine or Spermidine," *Arch. Biochem. Biophys.*, Vol. 137, pages 365–372 (1970)]. All of the alkylated norspermidine analogues have $IC_{50}$ values >100 $\mu$M at 48 hours. At 96 hours, the $IC_{50}$ values range from 3.5 to >100 $\mu$M with an order of DMNSPD<DENSPD<DPNSPD<MENSPD and MPNSPD (most to least active). Thus, in this family, terminal dialkylation with smaller groups increases the compound's activity, while triamines with a single alkyl group are less active than the corresponding compound with bis $N^\alpha,N^\omega$-alkyl substitution. In contrast, analogues of the tetraamine norspermine, although also inactive at 48 hours, were more active than the corresponding triamines at 96 hours. Moreover, whether norspermine was symmetrically substituted with methyl or ethyl groups or had a single ethyl fixed to one of the terminal nitrogens was insignificant relative to the 96-hour $IC_{50}$ values, which were around 2 $\mu$M.

At 48 hours, SPD and all of its analogues had an $IC_{50}$ of at least 100 $\mu$M. Unlike NSPD, and not surprisingly, SPD is the least active compound in its family with $IC_{50}$ values above 100 $\mu$M at both 48 and 96 hours. At 96 hours, DMSPD and DESPD are substantially more active than DPSPD. When an ethyl group was removed from either end of DESPD, a monoalkylated analogue was produced with lower activity than DESPD, by one to two orders of magnitude. It is interesting that monoalkylation of SPD by ethyl or propyl at different ends result in very different activities. At 96 hours, with an $IC_{50}$ of 4 $\mu$M, MESPD($N^1$) was about 10 times more active than MESPD($N^8$). The same trend was found, although to a lesser degree, among the two monopropyl SPD analogues in that MPSPD($N^1$) was more than twice as active as MPSPD($N^8$). Thus, alkylation at the $N^1$ position results in a higher activity than alkylation at $N^8$ (Table 1). The spermine analogues had a significant effect on cell growth even at 48 hours and at 96 hours, the $IC_{50}$ concentrations of tetraamines ranged from 0.2 to 0.8 $\mu$M, with DESPM<DPSPM<MESPM<DMSPM. Again, in every instance, the tetraamines were more active. It is interesting that 3.7% of intracellular $N^1$-MESPD and 6.1% of intracellular $N^1$-MPSPD are metabolically converted to the corresponding tetraamines, ME-[3,4,3] and MP-[3,4,3] respectively (Table 4). Given the potent antiproliferative activity of the tetraamines in general, this may help explain the enhanced activity of the $N^1$-alkylspermidines in comparison to the N8-alkylspermidines since the latter are not metabolically converted to tetraamines.

Among the HSPD analogues, DEHSPD is active at 48 hours with an $IC_{50}$ of 25 $\mu$M. Other analogues' $IC_{50}$s are at least 100 $\mu$M at 48 hours. At 96 hours, all of the $IC_{50}$s fall into the range from 0.3–0.9 $\mu$M, except for DPHSPD which has an $IC_{50}$ of 6 $\mu$M. Compared to the norspermidine and spermidine analogues, the homospermidine analogues as a group are more active. With the tetraamines, the most notable differences in activity were between the diethyl and dimethyl compounds (Table 1).

The (4,5) series are the most effective triamines identified. As the triamine chain increases in length from (4,5) to (5,5), the activity decreases at both 48 hours and 96 hours. Specifically, DM(4,5) and DE(4,5) have $IC_{50}$ values in the 2–6 $\mu$M range, while the DP(4,5) has an $IC_{50}$ around 100 $\mu$M at 48 hours. At 96 hours, the $IC_{50}$ values of both series substantially decrease; even DP(4,5) has an $IC_{50}$<2 $\mu$M. The numbers are uniformly higher for the (5,5) triamines even at 96 hours. The corresponding tetraamine analogues DE(4,5,4) and DE(5,4,5) are more active at both 48 and 96 hours.

Competitive Uptake Determinations in L1210 cells. The ability of the norspermidines, spermidines, homospermidines, 4,5- and 5,5-triamines to compete with radiolabeled SPD for uptake was evaluated (Table 1). The general trend is that the terminally alkylated triamines have higher $K_i$ values than the unalkylated triamines and are thus less easily taken up by the cell. In the dialkylated series of spermidines, homospermidines and 4,5-triamines, $K_i$ values increase as the size of the terminal group increases. This is not completely true with the norspermidines and the 5,5 triamines. The relationship holds with methyl and ethyl but not for the propyl of the latter two systems. Finally, the number of methylenes separating the amines plays a role in determining polyamine uptake properties. In general the effectiveness with which the analogues compete for uptake is spermidines≈homospermidines>4,5 triamines>5,5 triamines>norspermidine. Interestingly, this same trend is observed with the ethylated tetraamines, spermines≈homospermines>DE(3,4,4)≈DE(4,5,4) >norspermine.

TABLE 1

TRIAMINE ANALOGUE STRUCTURES, ABBREVIATIONS,
L1210 GROWTH INHIBITION AND TRANSPORT

| Structure | Abbreviation | IC$_{50}$ ($\mu$M) 48 hour | IC$_{50}$ ($\mu$M) 96 hour | K$_{i\ (\mu M)}$ |
|---|---|---|---|---|
| Norspermidines | | | | |
| 1 H$_2$N~~~N(H)~~~NH$_2$ | NSPD | 0.9 | 0.5 | 7.2 |
| 2 | DMNSPD | >100 (>100) | 3.5–6.0 (2.5) | 60 (5.6) |
| 3 | MENSPD | >100 (>100) | >100 (2.5) | 34 (7.7) |
| 4 | DENSPD | >100 (>100) | 10 (2) | 250 (17) |
| 5 | MPNSPD | >100 | ~100 | 33 |
| 6 | DPNSPD | >100 (>100) | 60 (18) | 125 (11) |
| Spermidine | | | | |
| 7 | SPD | >100 | >100 | 2.2 |
| 8 | DMSPD | >100 (>100) | 1.5–1.8 (0.75) | 5.1 (1.1) |
| 9 | MESPD(N1) | >100 (99) | 3.0–5.0 (0.33) | 8.6 (1.7) |
| 10 | MESPD(N8) | >100 | 40 | 7 |
| 11 | DESPD | ~100 (30) | 0.6–0.8 (0.18) | 19.3 (1.6) |
| 12 | MPSPD(N1) | >100 | 20–35 | 3.0 |
| 13 | MPSPD(N8) | >100 | 50–60 | 8.5 |
| 14 | DPSPD | >100 (3) | 30–35 (0.2) | 25.6 (2.3) |
| Homospermidines | | | | |
| 15 | HSPD | >100 | 1.7–4.0 | 3.4 |

TABLE 1-continued

TRIAMINE ANALOGUE STRUCTURES, ABBREVIATIONS,
L1210 GROWTH INHIBITION AND TRANSPORT

| Structure | Abbreviation | IC$_{50}$ ($\mu$M) 48 hour | IC$_{50}$ ($\mu$M) 96 hour | K$_i$ ($\mu$M) |
|---|---|---|---|---|
| 16 | DMHSPD | >100 (>100) | 0.9 (0.32) | 5.5 (0.97) |
| 17 | DEHSPD | 18–25 (0.2) | 0.3–0.4 (0.07) | 19 (1.4) |
| 18 | MPHSPD | 100 | 0.5–0.7 | 5.0 |
| 19 | DPHSPD | >100 | 6.0 | 67 |
| 4,5-triamines | | | | |
| 20 | 4,5-Triamine | >100 | 0.15–0.20 | 1.4 |
| 21 | DM(4,5) | 2.0 | 0.11–0.12 | 21 |
| 22 | DE(4,5) | 3.0–6.0 (0.3) | 0.19–0.2 (0.035) | 64 (6.0) |
| 23 | DP(4,5) | ~100 | 1.0–1.4 | 75 |
| 5,5-triamines | | | | |
| 24 | 5,5-Triamine | ~100 | 0.3–0.5 | 13.8 |
| 25 | DM(5,5) | 15 | 0.4 | 133 |
| 26 | DE(5,5) | 10–12 (0.4) | 0.65–0.7 (0.03) | 174 (16) |
| 27 | DP(5,5) | >100 | 6.0 | 87 |

$K_i$ values and IC$_{50}$ concentrations at 48 and 96 hours. $K_i$ determinations were made by following analogue inhibition of spermidine transport. The IC$_{50}$ and $K_i$ values of corresponding tetraamine analogues are shown in parentheses. The tetraamine corresponding to DE(4,5) (22) is DE(4,5,4), and the tetraamine corresponding to DE(5,5) (26) is DE(5,4,5) (29).

Polyamine Pools. The following guidelines were adopted for studying the impact of the analogues on polyamine pools (Table 2). The measurements were made after a 48-hour exposure to the analogue, and two different concentrations of analogue were evaluated in each case. For analogues whose IC$_{50}$ concentration exceeded 100 $\mu$M at 48 hours, the polyamine pools were determined at 100 and 500 $\mu$M. For the other analogues, the effect on polyamine pools was evaluated at the 48-hour IC$_{50}$ concentration and at 5 times this number.

At 500 $\mu$M, the effects of DMNSPD, DENSPD and MPNSPD on polyamine pools were similar (Table 2), i.e., PUT was depleted below detectable limits and spermidine was reduced to 6–15% of controls, while spermine levels were diminished to below 50%. DPNSPD was not as effective as the other norspermidine analogues in depletion of polyamine pools, e.g., at 500 µM, PUT was only lowered to 68%, SPD to 71% and no effect on SPM level. The dipropyl analogue was similar in behavior to the parent norspermidine. The corresponding norspermines were again more effective. At 100 µM, the effect of DMNSPM and DENSPM on polyamine pools was similar, i.e., putrescine was depleted to below detectable limits and spermidine was reduced to around 5% of controls, while spermine levels were diminished to 27–36%.

DMSPD and DESPD at 100 µM depleted PUT to below detectable limits, SPD to 5%, SPM to 58% and 74% of control, respectively. The monoalkylated SPD analogues MESPD($N^1$), MESPD($N^8$) and MPSPD($N^1$) gave a similar pattern of polyamine pool depletion. At 100 µM, putrescine was depleted to below detectable levels, spermidine to 25% and spermine to 80%, 84% and 90% of control value. MPSPD($N^8$) was slightly less active than MPSPD($N^1$). At 500 µM, DPSPD reduced PUT to below detectable level and SPD to around 10% of control. Like DPNSPD, DPSPD showed little suppression of SPM levels and possibly even some up-regulation at 100 µM. Interestingly, at the level of PUT and SPD suppression, MPSPD ($N^1$) and MPSPD ($N^8$) behave very much like their MESPD counterparts. However, the propyl analogues are slightly less effective at spermine suppression. The parent amine SPD suppresses PUT, but not SPD or SPM. Again, the corresponding spermines are more effective than the triamines. At 100 or 500 µM DMSPM or MESPM or at 30 and 150 µM DESPM, putrescine was reduced to below detectable limits, spermidine diminished to under 2% of control and spermine to under 25%. At 3 µM, DPSPM reduced putrescine to below detection and spermidine to 18%, while the spermine level remained at 64% of control. At 15 µM DPSPM, spermidine was further reduced to 9% and spermine to 43%.

Among the homospermidine analogues, the parent triamine, HSPD, was the most active at polyamine suppression. At 100 µM, PUT was depleted to again below detectable levels, SPD to 4% and SPM to 32%. With all of the HSPD analogues, at 500 µM, the level of putrescine was diminished to below detectable limits and the SPD level below 10% of control. DMHSPD and DEHSPD had little impact on SPM level, while MPHSPD produced a mild decrease. In the case of cells grown in 100 µM and 500 µM DPHSPD, the level of SPM seemed to be increased compared to the controls. As is usual, the homospermines were more effective than the corresponding triamine counterparts. At 100 µM, the homospermine analogue DMHSPM was similar to the corresponding alkyl spermine in its ability to deplete the polyamines. However, DEHSPM was somewhat less effective at suppressing spermine pools in comparison to DESPM.

Similar results were observed with homospermidine homologues, the (4,5) and (5,5) triamines. At 500 µM, the (4,5) and (5,5) parent amines depleted both PUT and SPD below detectable level and SPM to 35% and 20% of control, respectively. DM(4,5) at 10 µM and DE(4,5) at 15 µM reduce PUT below detectable limits and SPD to 18% of control. However, neither is very effective at reducing SPM levels. DP(4,5) even at 500 µM, while it depletes the cell of PUT, only reduces SPD to 31% of control with possible stimulation of SPM. Finally, DP(5,5) is only marginally active, requiring a 500 µM concentration to even reduce PUT by 50% and SPD by 30% and with no impact on SPM. However, the homospermine homologues DE(4,5,4) and DE(5,4,5), both of which demonstrated low 48-hour $IC_{50}$ values, 0.3 and 0.4 µM, respectively, were similar to the corresponding triamines at reducing polyamines.

TABLE 2

IMPACT OF TRIAMINE ANALOGUES ON POLYAMINE POOLS[a]

| Compd | Conc. (µM) | Put | Spd | Spm | Analogue[b] |
|---|---|---|---|---|---|
| Norspermidines | | | | | |
| 1 NSPD | 0.9 | 38 | 44 | 113 | 1.09 |
|  | 45 | 0 | 12 | 83 | 2.14 |
| 2 DMNSPD | 100(100) | 0(0) | 9(5) | 58(36) | 5.00(2.14) |
|  | 500(500) | 0(0) | 6(3) | 48(27) | 5.51(1.84) |
| 4 DENSPD | 100 (10) | 0(30) | 17(14) | 74(31) | 3.67(1.59) |
|  | 500(100) | 0(0) | 7(6) | 47(30) | 3.77(2.44) |
| 5 MPNSPD | 100 | 0 | 29 | 56 | 3.07 |
|  | 500 | 0 | 15 | 49 | 4.78 |
| 6 DPNSPD | 100(100) | 70(61) | 76(35) | 96(77) | 0.49(0.89) |
|  | 500(500) | 68(0) | 71(19) | 102(56) | 1.24(1.28) |
| Spermidines | | | | | |
| 7 SPD | 100 | 0 | 117 | 118 | — |
|  | 500 | 0 | 145 | 108 | — |
| 8 DMSPD | 100(100) | 0(0) | 5(0) | 58(21) | 4.96(1.26) |
|  | 500(500) | 0(0) | 0(0) | 54(24) | 4.89(1.24) |
| 9 MESPD(N1) | 100(160) | 0(0) | 25(1) | 80(21) | 4.20(1.24) |
|  | 500(500) | 0(0) | 14(1) | 53(19) | 4.73(1.23) |
| 10 MESPD(N8) | 100 | 0 | 26 | 84 | 4.41 |
|  | 500 | 0 | 15 | 61 | 4.96 |
| 11 DESPD | 100(30) | 0(0) | 5(0) | 74(12) | 4.61(0.40) |
|  | 500(150) | 0(0) | 0(0) | 55(14) | 4.20(1.13) |
| 12 MPSPD(N1) | 100 | 0 | 25 | 90 | 3.97 |
|  | 500 | 0 | 15 | 72 | 4.95 |
| 13 MPSPD(N8) | 100 | 0 | 33 | 103 | 3.52 |
|  | 500 | 0 | 16 | 95 | 5.16 |
| 14 DPSPD | 100(3) | 6(0) | 35(18) | 135(64) | 3.26(1.12) |
|  | 500(15) | 0(0) | 12(9) | 99(43) | 3.69(1.09) |
| Homospermidines | | | | | |
| 15 HSPD | 100 | 0 | 4 | 32 | 3.58 |
|  | 500 | 0 | 2 | 21 | 4.44 |
| 16 DMHSPD | 100(100) | 0(0) | 3(0) | 106(30) | 5.51(1.49) |
|  | 500(500) | 0(0) | 0(0) | 106(27) | 5.85(1.03) |
| 17 DEHSPD | 25(10) | 0(0) | 6(0) | 114(61) | 4.61(2.94) |
|  | 125 | 0 | 3 | 97 | 4.69 |
| 18 MPHSPD | 100 | 0 | 2 | 82 | 5.16 |
|  | 500 | 0 | 0 | 66 | 5.86 |
| 19 DPHSPD | 100 | 0 | 19 | 144 | 3.12 |
|  | 500 | 0 | 7 | 111 | 3.68 |
| 4,5-Triamines | | | | | |
| 20 4,5 | 100 | 0 | 1 | 53 | 3.02 |
|  | 500 | 0 | 0 | 35 | 3.20 |
| 21 DM(4,5) | 2 | 0 | 33 | 112 | 2.79 |
|  | 10 | 0 | 18 | 111 | 5.36 |
| 22 DE(4,5) | 3(0.3) | 0(44) | 47(61) | 99(70) | 1.20(0.26) |
|  | 15(1.5) | 0(0) | 18(5) | 98(31) | 3.40(0.72) |
| 23 DP(4,5) | 100 | 0 | 40 | 119 | 1.40 |
|  | 500 | 0 | 31 | 121 | 2.42 |
| 5,5-Triamines | | | | | |
| 24 5,5 | 100 | 0 | 0 | 33 | 2.58 |
|  | 500 | 0 | 0 | 20 | 2.50 |
| 25 DM(5,5) | 15 | 0 | 33 | 115 | 2.56 |
|  | 75 | 0 | 20 | 101 | 3.61 |
| 26 DE(5,5) | 15(0.15) | 0(37) | 55(55) | 97(88) | 1.09(0.34) |
|  | 75(0.75) | 0(0) | 23(10) | 73(58) | 1.59(1.48) |
| 27 DP(5,5) | 100 | 59 | 73 | 97 | 0.86 |
|  | 500 | 51 | 69 | 103 | 1.33 |

[a] Putrescine (Put), spermidine (Spd) and spermine (Spm) Levels after 48 hours of treatment are given as % polyamine found in untreated controls. Typical control values in pmol/$10^6$ L1210 cells are Put=260±59, Spd 3354±361, Spm=658±119.

[b] Analogue amount is expressed as nmol/10[6] cells. Untreated L1210 cells (10[6]) correspond to about 1 μL volume; therefore, concentration can be estimated as nmol/mM.

Impact of Analogues on ODC and AdoMetDC Activities. A comparison of the effects of the triamine versus tetraamine polyamine analogues on ODC and AdoMetDC clearly demonstrates that the tetraamines are more effective at suppressing these enzymes than the corresponding triamines [Bergeron et al, *J. Med. Chem.*, Vol. 37, supra]. Previous studies [Porter et al, "Regulation of Ornithine Decarboxylase Activity by Spermidine and the Spermine Analogue $N^1,N^8$-Bis(ethyl)spermidine," *Biochem. J.*, Vol. 242, pages 433–440 (1987); and Porter et al, "Combined Regulation of Ornithine and S-Adenosylmethionine Decarboxylase by Spermine and the Spermine Analogue $N^1,N^2$-Bis(ethyl)spermine," *Biochem. J.*, Vol. 268, pages 207–212 (1990)] suggested that the effect of the polyamine analogues on ODC and AdoMetDC is fairly rapid. For example, DESPM induced reduction in ODC activity plateaued at 4 hours and AdoMetDC at 6 hours. On the basis of these studies, it was elected to evaluate the impact of the triamines on ODC and AdoMetDC at 4 and 6 hours, respectively.

The parent triamine norspermidine reduced ODC activity to 11% of control, the corresponding dimethyl, DMSPD, to 17%, the diethyl analogue, DENSPD, to 80% and the dipropyl compound, DPNSPD, had no effect on this enzyme (Table 3). Monoethylnorspermidine, MENSPD, was more active than the corresponding dialkyl analogue, DENSPD, with reduction to 42 versus 80% of control, as was the monopropyl, MPNSPD, relative to its dipropyl counterpart DPNSPD, with reduction to 33 versus 100% of control. In 4 hours, 1 μM DMNSPM, MENSPM or DENSPM reduced ODC activity to nearly the same extent, to approximately 7% of control. The triamines are generally less effective than the corresponding tetraamines at suppressing AdoMetDC, although the differences are not as profound with the norspermidines versus the norspermines. The norspermidines reduce the AdoMetDC to 41–58% of control and the norspermines to 33–49% of control, except the dipropyls, which are at best marginally effective.

The spermidine analogues are less active than the corresponding spermines but more effective at reducing ODC activity than the norspermidines. At 1 μM DMSPM, MESPM or DESPM, ODC activity was reduced to 10% or less of control, while ODC in DPSPM-treated cells was only lowered to 52% of controls. The parent triamine spermidine reduces ODC to 16% of control while the alkylated analogues except for DPSPD, diminish ODC activity to between 10–30% of control. Again, the monoalkyl analogues are more effective than the corresponding dialkyl compounds. MESPD($N^1$) and MESPD($N^8$) reduce ODC to 10 and 17% versus 30% for DESPD. This property of the monoalkylated analogue is even further accentuated with the propylated spermidines MPSPD($N^1$) and MPSPD($N^8$) versus DPSPD lowering ODC to 18 and 14% versus 75% of control. Again, when comparing dialkylated compounds, the larger the alkyl substituent the less active the analogue.

The spermidine analogues were less effective than the corresponding norspermidines and spermines at reducing AdoMet activity. The spermidine analogues, except for DPSPD, reduce AdoMetDC to under 70% of control activity. DPSPD has no impact on the enzyme. Again, as with ODC, the monoalkylated spermidine compounds were generally more active than the dialkylated compounds.

DMSPM, MESPM or DESPM at 1 μM almost paralleled the ability of the corresponding norspermine analogues to suppress AdoMetDC with an average reduction to 33% of control, slightly more active than the spermidines. DPSPM at 1 μM reduced AdoMetDC activity to 72% of that seen in untreated cells.

The homospermidines were less active than the corresponding homospermines at reducing ODC activity, but similar in behavior to the spermidines. Also, consistent with the norspermidine and spermidine results, the triamines with the larger substituent, propyl, were least effective and the monoalkyl compounds were more active than the corresponding dialkyl ones. Finally, the homospermidine analogues, except for MPHSPD, were not effective at AdoMetDC inhibition and certainly less active than the corresponding tetraamines.

Interestingly, adding a methylene unit to DEHSPM to produce DE(4,5,4) resulted in a decrease in ODC suppressing activity. ODC was lowered to only 7% of control with DEHSPM and to 20% of control with DE(4,5,4). This methylene addition had little effect on reduction of AdoMetDC activity, to about 40% for both. The same phenomenon was observed on moving from lower alkylhomospermidines to the dialkyl (4,5) and dialkyl (5,5) compounds, the ODC-suppressing capacity substantially decreased while the AdoMetDC properties were similar to those of the homospermidines. It is noteworthy, however, that the parent (4,5)-triamine demonstrates reasonably effective suppression of ODC and AdoMetDC. The (5,5) parent triamine is an effective and highly selective ODC antagonist, reducing ODC to 16% of control with little effect on AdoMetDC. Other than this, there is little effect on either ODC or AdoMetDC by (5,5) analogues. The tetraamine analogue DE(5,4,5) is far more active against both ODC and AdoMetDC than DE(5,5).

Figure 6A:
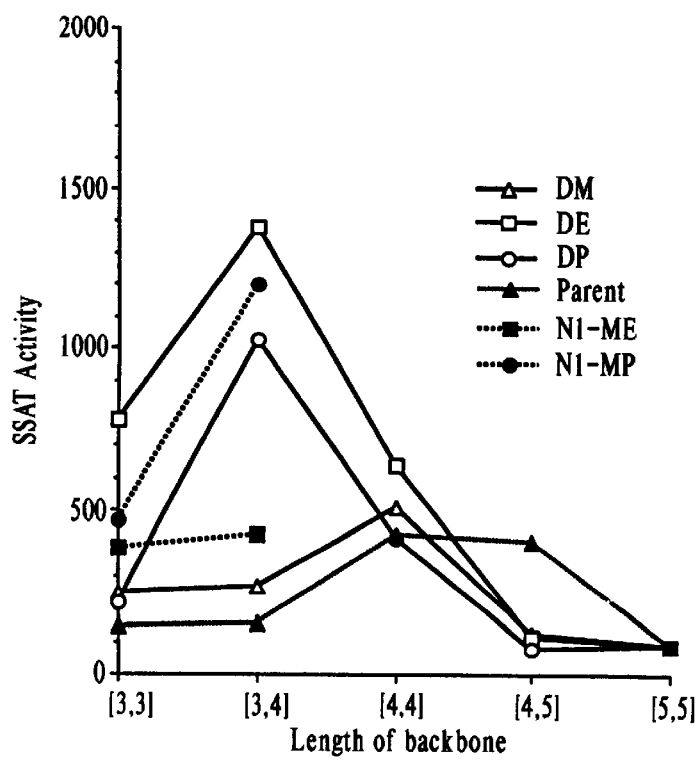
FIGS. 6(*a*) and 6(*b*) depict the structure-activity relationship between triamine analogues and tetraamine analogues, respectively, and SSAT up-regulation.
Figure 6B:
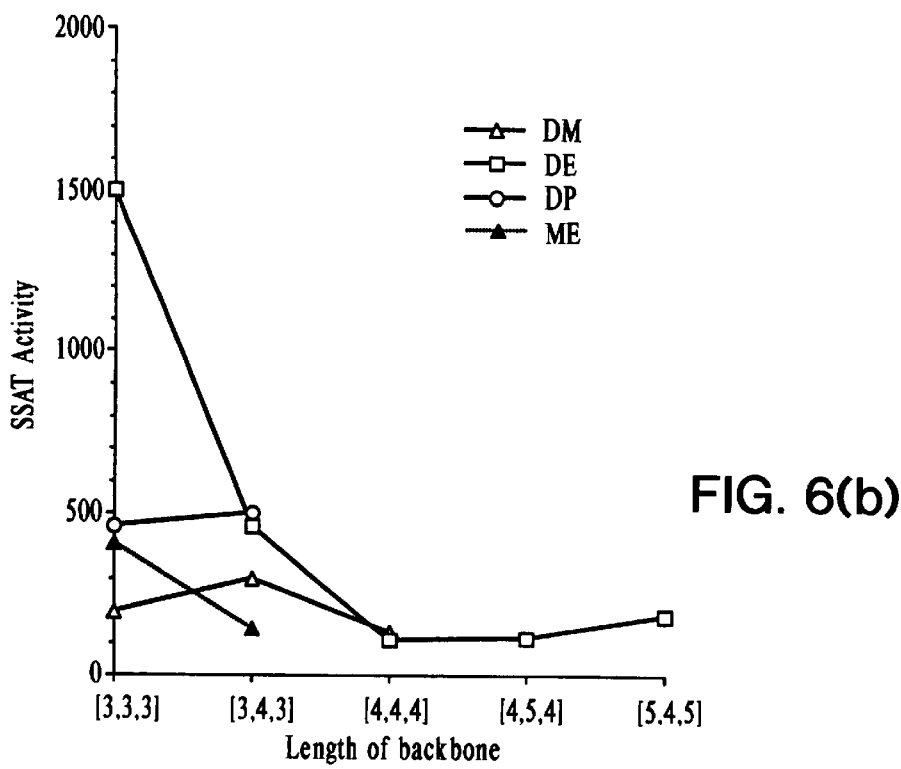

Impact of Triamine Analogues on SSAT Activity. While the influence of chain length and terminal substituents are more monotonic regarding their effect on the analogues' suppression of ODC and AdoMetDC, there are nevertheless some notable structure-activity relationships for SSAT stimulation. The ability of triamine analogues to up-regulate SSAT in L1210 cells is remarkably sensitive to small structural changes (Table 3; FIG. 6a). For example, the diethyl triamines stimulate SSAT 780% for DE(3,3) to a peak of 1380% for DE(3,4), with a decrease to 640% for DE(4,4) and falling to essentially control values for DE(4,5), 120%, and DE(5,5), 90%. The DE triamine structure activity curve appears to be shifted to the right from the corresponding DE tetraamine curve (FIG. 6b). Thus, the DE tetraamine curve is maximal at 1500% of control for DE(3,3,3) and falls to nearly control value for DE(4,4,4), DE(4,5,4) and DE(5,4,5).

Substituent changes on the triamines have a profound effect on SSAT stimulation only with the (3,3) and (3,4) compounds. The differences are more compressed for the (4,4) and (4,5) triamines and absent with (5,5) triamines. In the case of the tetraamines, the (3,3,3) system is the only framework in which a marked effect in SSAT stimulation is observed with substituent changes. While there are some changes with the (3,4,3) backbone, these are again compressed.

With both the triamines and tetraamines, unlike with ODC and AdoMetDC, there is no relationship between substituent size and SSAT up-regulation. However, when clear differences exist between stimulatory abilities, i.e., (3,3), (3,4), (3,3,3), the ethyl group is clearly the superior.

TABLE 3

EFFECT OF POLYAMINE HOMOLOGUES ON
ORNITHINE DECARBOXYLASE (ODC),
S-ADENOSYLMETHIONINE DECARBOXYLASE (AdoMetDC)
AND SPERMIDINE/SPERMINE ACETYLTRANSFERASE (SSAT)
IN L1210 CELLS

|  | Compd | ODC | AdoMetDC | SSAT |
|---|---|---|---|---|
|  | Norspermidines | | | |
| 1 | NSPD | 11 | 62 | 150 |
| 2 | DMNSPD | 17(6) | 41(49) | 250(200) |
| 3 | MENSPD | 42(5) | 58(33) | 390(410) |
| 4 | DENSPD | 80(10) | 45(42) | 780(1500) |
| 5 | MPNSPD | 33 | 38 | 470 |
| 6 | DPNSPD | 100(79) | 99(70) | 220(460) |
|  | Spermidines | | | |
| 7 | SPD | 16 | 43 | 160 |
| 8 | DMSPD | 22(3) | 68(40) | 270(300) |
| 9 | MESPD(N1) | 10(10) | 58(27) | 430(150) |
| 10 | MESPD(N8) | 17 | 54 | 400 |
| 11 | DESPD | 30(3) | 68(28) | 1380(460) |
| 12 | MPSPD(N1) | 18 | 56 | 1200 |
| 13 | MPSPD(N8) | 14 | 64 | 500 |
| 14 | DPSPD | 75(52) | 107(72) | 1030(500) |
|  | Homospermidines | | | |
| 15 | HSPD | 11 | 54 | 430 |
| 16 | DMHSPD | 20(4) | 86(45) | 510(140) |
| 17 | DEHSPD | 47(7) | 90(41) | 640(110) |
| 18 | MPHSPD | 20 | 59 | 570 |
| 19 | DPHSPD | 86 | 123 | 420 |
|  | 4,5-triamines | | | |
| 20 | 4,5-triamine | 19 | 57 | 410 |
| 21 | DM(4,5) | 56 | 71 | 130 |
| 22 | DE(4,5) | 100(20) | 70(39) | 120(120) |
| 23 | DP(4,5) | 83 | 86 | 80 |
|  | 5,5,triamines | | | |
| 24 | 5,5-triamine | 16 | 88 | 90 |
| 25 | DM(5,5) | 105 | 97 | 90 |
| 26 | DE(5,5) | 100(19) | 109(54) | 90(190) |
| 27 | DP(5,5) | 73 | 123 | 90 |

Enzyme activity is expressed as percent of untreated control for ODC (1 $\mu$M at 4 hours), AdoMetDC (1 $\mu$M at 6 hours) and SSAT (10 $\mu$M at 48 hours for triamine analogues, and 2 $\mu$M at 48 hours for tetraamine analogues). The ODC, AdoMetDC and SSAT levels of corresponding tetraamine analogues are shown in parentheses.

Metabolism. In an experiment focused on the impact of DPNSPD (DP-[3,3] in Table 4) on polyamine pools, a substantial unexpected peak appeared in the chromatogram of treated cells. The suspicious peak was shown to correspond to MPNSPD (MP-[3,3] in Table 4) as confirmed by co-elution with an authentic sample. The intracellular levels of MPNSPD after a 48-hour exposure to DPNSPD was about 50% of intracellular level of the parent compound. Although N-dealkylation had been shown to be an important step in the metabolism of the alkylated tetraamines DENSPM [Bergeron et al, *Drug Metab. Dispos.*, Vol. 23, supra] and DEHSPM [Bergeron et al, "Metabolism and Pharmacokinetics of $N^1,N^{14}$-Diethylhomospermine," *Drug Metab. Dispos.*, Vol. 24, pages 334–343 (1996)] in vivo in rodents, dogs and man, previous in vitro studies with DEHSPM or DESPM [Bergeron et al, *J. Med. Chem.*, Vol. 37, supra] in L1210 cells revealed either little or no N-dealkylation under the conditions of the experiments. The observation of N-depropylation of DPNSPD compelled a closer look at the metabolism of the polyamine analogues in L1210 cells. In particular, the significance of the nature of the N-alkyl groups on N-dealkylation was evaluated, in addition to the length and symmetry of the polyamine backbone.

TABLE 4

METABOLIC TRANSFORMATION OF POLYAMINE ANALOGUES BY L1210 CELLS

| Analog# | | N-Monodealkylation ^ | | | | Deaminopropylation ^ | | Elaboration ^ |
|---|---|---|---|---|---|---|---|---|
| DM-[3,3] (100 $\mu$M) | 5000(100%) | no N-demethylation | | | | | | |
| MM-[3,3,3] (100 $\mu$M) | 2633(82.9%) | no N-demethylation | | | | MM-[3,3] | 523(16.5%) | MM-[3]** 20(0.6%) |
| DE-[3,3,3] (500 $\mu$M) | 2440(95.3%) | ME-[3,3,3] | 194(4.7%) | | | | | |
| DE-[3,3] (500 $\mu$M) | 3761(90.7%) | ME-[3,3] | 194(4.7%) | | | ME-[3] | 192(4.6%) | |
| ME-[3,3] (100 $\mu$M) | 3051(78.2%) | [3,3] | 20(0.5%) | | | ME-[3] | 831(21.3%) | no elaboration of N-Monoalkyl [3,3] |
| DP-[3,3,3] (100 $\mu$M) | 893(78.2%) | MP-[3,3,3]* | 160(14.0%) | | | MP-[3,3] | 89(7.8%) | |
| DP-[3,3] (100 $\mu$M) | 404(57.7%) | MP-[3,3] | 214(30.6%) | [3,3]*** | 64 (9.1%) | MP-[3]* | 18(216%) | |
| MP-[3,3] (100 $\mu$M) | 3019(94.3%) | [3,3] | 144(4.5%) | | | MP-[3]* | 37(1.2%) | no elaboration of N-Monoalkyl [3,3] |
| DM-[3,4] (100 $\mu$M) | 5000(100%) | no N-demethylation | | | | | | |
| DE-[3,4] (100 $\mu$M) | 4041(96.3%) | N8-ME-[4,3] | 32(0.8%) | N1-ME-[3,4] | 101 (2.4%) | | | |
| N1-ME-[3,4] | 3946(96.3%) | [3,4] | not determined | | | | | ME- 150 |

TABLE 4-continued

METABOLIC TRANSFORMATION OF POLYAMINE ANALOGUES BY L1210 CELLS

| Analog# | | | N-Monodealkylation^ | | | Deaminopropylation^ | | Elaboration^ |
|---|---|---|---|---|---|---|---|---|
| (100 µM) | | | | | | | | [3,4,3] (3.7%) |
| N8-ME-[4,3] | 4825(99.4%) | [3,4] | not determined | | | ME-[4] | 29(0.6%) | no elaboration of |
| (100 µM) | | | | | | | | N8-Alkyl [4,3] |
| DP-[3,4,3] | 1568(79.0%) | MP-[3,4,3]* | 361(18.2%) | | | N1-MP-[3,4] | 57(2.9%) | |
| (15 µM) | | | | | | | | |
| DP-[3,4] | 3260(90.1%) | N8-MP-[4,3] | 192(5.3%) | N1-MP-[3,4] | 166 (4.6%) | | | |
| (100 µM) | | | | | | | | |
| N1-MP-[3,4] | 4238(93.9%) | [3,4] | not determined | | | | | MP-[3,4,3] 275 (6.1%) |
| (100 µM) | | | | | | | | |
| N8-MP-[4,3] | 3549(99.3%) | [3,4] | not determined | | | MP-[4]* | 26(0.7%) | no elaboration of N8-Alkyl [4.3] |
| (100 µM) | | | | | | | | |
| DM-[4,4] | 5500(100%) | | no N-demethylation | | | no exposed primary aminopropyl terminal segment | | |
| (100 µM) | | | | | | | | |
| DE-[4,4,4] | 4215(100%) | | no N-deethylation | | | " | | |
| (100 µM) | | | | | | | | |
| DH-[4,4] | 4215(100%) | | no N-deethylation | | | " | | |
| (100 µM) | | | | | | | | |
| DP-[4,4] | 3149(87.7%) | MP-[4,4] | 441(12.3%) | | | " | | no elaboration of N-Monoalkyl [4,4] |
| (500 µM) | | | | | | | | |
| DM-[4,5] | 2790(100%) | | no N-demethylation | | | no exposed primary aminopropyl terminal segment | | |
| (2 µM) | | | | | | | | |
| DE-[4,5] | 4215(100%) | | no N-deethylation | | | " | | |
| (100 µM) | | | | | | | | |
| DP-[4,5] | 1325(69.7%) | N1-MP-[5,4]* | 576(30.0%) | | | " | | no elaboration of N-Monoalkyl [5,4] |
| (100 µM) | | | | | | | | |
| DM-[5,5] | 2560(100%) | | no N-demethylation | | | no exposed primary aminopropyl terminal segment | | |
| (15 µM) | | | | | | | | |
| DE-[5,5] | 1585(100%) | | no N-deethylation | " | | | | |
| (75 µM) | | | | | | | | |
| DP-[5,5] | 1300(100%) | | no N-depropylation | " | | | | |
| (80 µM) | | | | | | | | |

\# L1210 cells were grown 46 hours in medium containing polyamine analogue at the indicated concentration. Then the polyamine contents of the cells were analyzed by HPLC of the fluorescent DANSYL derivatives.
^ Concentrations of parent drug and metabolites in L1210 cells are in pmols/$10^6$ and as % of total drug in the cell.
*An authentic sample of these presumed metabolites was not available for analytical reference. All other metabolites were identified and quanititaed by comparison to authenticated reference compounds.
**Formed by deaminopropylation of primary metabolite MM-[3,3].
***Formed by N-depropylation of MP-[3,3].

In order to assure that the observation was not some artifact of the experimental conditions, it was assessed whether or not components of the culture media itself were responsible for dealkylation (Table 5). Fetal bovine serum (FBS), for example, is well known to contain amine oxidases [Morgan, "Polyamine Oxidases and Oxidized Polyamines," Chapter 13 in *The Physiology of Polyamines*, Vol. I; Bachrach et al, eds., CRC Press: Boca Raton, Fla. (1989), pages 203–229]. Indeed, 1 mM aminoguanidine, an inhibitor [Gahl et al, "Reversal by Aminoguanidine of the Inhibition of Proliferation of Human Fibroblasts by Spermidine and Spermine," *Chem.-Biol. Interactions*, Vol. 22, pages 91–98 (1978)] of bovine serum amine oxidase present in the standard L1210 cell culture media, did not totally eliminate such FBS-related amine oxidase activity. When the "complete" RPMI-40 medium containing FBS and 1 mM aminoguanidine was incubated in the presence of 100 or 500 µM DPNSPD, a small amount (<3%) of the DPNSPD was metabolized to MPNSPD in the absence of L1210 cells. This corresponds to a comparatively low extracellular concentration of MPNSPD (~3 µM) and, given its relatively poor affinity ($K_t$=33 µM) for the polyamine transport apparatus, argues against the extracellular medium as a major source of the high levels of MPNSPD (264 µM) seen intracellularly. This conclusion is further supported by experiments which partially or totally eliminate the source of extracellular metabolism. For example, when FBS was replaced with either NuSerum, a semi-synthetic substitute, or purified bovine serum albumin, a high level of intracellular metabolite (50% of parent analogue, Table 5) was still observed. The chelator bathophenanthroline disulfonic acid is a well-known inhibitor of the Cu-dependent amine oxidases present in plasma [Frieden, "Complex Copper of Nature," *Metamorphosis, A Problem in Developmental Biology*, 2nd ed., Gibert et al, eds., Plenum Press: New York, N.Y., pages 478–483 (1981)] and, given its comparatively high MW and anionic charge, does not cross the cell membrane [Alcain et al, "Iron Reverses Impermeable Chelator Inhibition of DNA Synthesis in CCl39 cells," *Proc. Natl. Acad. Sci. U.S.A.*, Vol. 91, pages 7903–7906 (1994); and Glahn et al, "Bathophenanthroline Disulfonic Acid and Sodium Dithionite Effectively Remove Surface-Bound Iron from $CaCO_2$ Cell Monolayers," *J. Nutr.*, Vol. 125, pages 1833–1840 (1995)]. As expected, bathophenanthroline disulfonic acid completely abolished the ability of RPMI-40+ 10% FBS to convert DPNSPD to MPNSPD. However, when cells were grown in RPMI-containing FBS and bathophenanthroline disulfonic acid, high intracellular concentrations of MPNSPD corresponding to ca. 50% of the intrac ellular DPNSPD content were observed. These results are in keeping with the idea that the dealkylation indeed takes place within L1210 cells.

TABLE 5

METABOLISM OF DPNSPD IN DIFFERENT CULTURE SYSTEMS

| Assay # | Experiment Treatments | Metabolites (% of DPNSPD) |
|---|---|---|
| 1 | FBS[a] + L1210 (48 hours) | MPNSPD (50%) |
| 2 | NuSerum[a] + L1210 (48 hours) | MPNSPD (50%) |
| 3 | FBS (48 hours) | MPNSPD (3%) |
| 4 | Albumin[b] + L1210 (4 hours) | MPNSPD (50%) |
| 5 | FBS + bathophenanthroline disulfonic acid (0.1 mM) (48 hours) | MPNSPD (0%) |
| 6 | FBS + L1210 + bathophenanthroline disulfonic acid (0.1 mM) (48 hours) | MPNSPD (50%) |

In all of the assays, RPMI-1640 was used as culture media. NuSerum IV is a semi-synthetic FBS substitute, containing 25% of FBS. [a] At concentration of 10%. [b] At concentration of 1.5%.

Assured that what was being seen were the results of intracellular metabolic transformation of bisalkylated triamines, an examination of the influence of polyamine analogue structure on the metabolite pattern observed in L1210 cells was undertaken. These results are detailed in Table 4 for the bisalkyl triamines and a number of their primary metabolites. Several representative tetraamine analogues are also included to demonstrate their similar metabolic fate to the corresponding triamines. Note, too, that the structures are depicted with the polyamine backbone described as Arabic numerals separated by commas so that the numeral represents the number of methylenes in the linear alkane sections separating amine centers, thus [3,3]= NSPD, [3,4,3]=SPM, [4]=putrescine, and so forth.

Three types of metabolic transformations explain the particular patterns observed (FIG. 7). First, bisalkyl polyamines must undergo N-dealkylation before any further metabolism can occur. If this N-dealkylation results in exposure of a primary aminopropyl segment, the primary metabolite(s) may undergo deaminopropylation by the SSAT/PAO polyamine degradation pathway. If this N-dealkylation results in exposure of a primary aminobutyl segment, then the triamine might undergo elaboration into a tetraamine by serving as a substrate for spermine synthase, which anneals an aminopropyl segment derived from S-adenosylmethionine (AdoMet) to the free aminobutyl end of the molecule. Below, the evidence as revealed in the metabolite patterns that support these three types of metabolic transformations is detailed, along with comments on the implications these data have with respect to the structural requirements of the corresponding enzyme systems in vivo.

A careful inspection of chromatograms from cells treated with DM-[3,3], DM-[3,4], DM-[4,4], DM-[4,5] and DM-[5,5] revealed no N-demethylation (Table 4). The dimethyl tetraamines DM-[3,3,3], DM-[3,4,3] and DM-[4,4,4] also showed no evidence of N-dealkylation (data not shown), and the unsymmetric tetraamine MM-[3,3,3] is only metabolized by deaminopropylation at the primary amine terminus end of the molecule.

Treatment of cells with DE-[3,3] or the corresponding tetraamine, DE-[3,3,3], each resulted in the monodeethylated metabolite, ME-[3,3] or ME-[3,3,3], respectively, in similar amounts: 4.7% on a mole percent basis of the total (parent drug+identified metabolites) in the cell. Interestingly, cells treated with the unsymmetric DE-[3,4] contain each of the two possible monodeethylated metabolites, N1-ME-[3,4] and N8-ME-[4,3] with the total amount representing about 4% of the drug in the cell. Among the diethylated triamine analogues, only DE-[3,3] and DE-[3,4] showed N-deethylated metabolite(s); the analogues with longer backbones, i.e., DE-[4,4], DE-[4,5] and DE-[5,5], do not show significant N-deethylation at all.

Of the five different dipropyl triamines which were evaluated, DP-[3,3], DP-[3,4], DP-[4,4], DP-[4,5] and DP-[5,5], all but DP-[5,5] showed significant N-depropylation. As suggested from the quantity of analogue present in cells as monodealkylated metabolite (Table 4), N-depropylation in general occurs to a greater extent than N-deethylation. For example, in L1210 cells treated with DP-[3,3], 57.7% is present as the parent drug, DP-[3,3], 30.6% as the mono-N-dealkylated metabolite, MP-[3,3], 9.1% as the di-N-dealkylated metabolite, [3,3], and 2.6% as the secondary metabolite, MP-[3], formed by deaminopropylation of MP-[3,3]. The same general pattern holds for cells treated with the corresponding tetraamine, DP-[3,3,3], where 14.0% of the total is present as MP-[3,3,3] and 7.8% as MP-[3,3] formed by secondary deaminopropylation of MP-[3,3,3]. Cells treated with the corresponding diethyl analogues contain substantially lower amounts of metabolites by comparison so that 90.7% of DE-[3,3] or 95.3% of DE-[3,3,3] is present as the unmetabolized parent compound.

The dipropyl triamine with the shortest backbone DP-[3,3] seemed most sensitive to metabolism with MP-[3,3] representing 31% of the total drug. With DP-[3,4], both possible monoalkylated products N1-MP-[3,4] and N8-MP-[4,3] were detected at levels corresponding to 4.6% and 5.3%, respectively, of the total drug in the cell. Cells exposed to DP-[4,4] contained the mono-N-dealkylated metabolite, MP-[4,4], representing 12.3% of the total drug in the cell. Interestingly, only one of the two possible N-dealkylated metabolites was apparent in cells treated with the unsymmetric triamine DP-[4,5], and this MP-[5,4] metabolite represented 32.9% of the total drug in the cell. When DP-[5,5] was evaluated, no metabolic products were found, suggesting that the aminobutyl end of DP-[4,5] system was selectively dealkylated to form the monodealkylated metabolite, N10-MP-[5,4].

If mono-N-dealkylation exposes a primary aminopropyl terminus, this compound is subject to further metabolism by the SSAT/PAO system present in all cells. First, SSAT acetylates the exposed primary amine end, then PAO oxidatively deaminates at the interior secondary amino nitrogen of the acetamidopropylamine segment to give acetamidopropanal, i.e., net deaminopropylation of the substrate. PAO actively deaminopropylates $N^1$-acetylspermine and $N^1$-acetylspermidine, the native substrates, but does not recognize the acetamidobutyl segment of $N^8$-acetylspermidine or N-acetylputrescine as substrate. Table 4 demonstrates that, in L1210 cells, there is a strict adherence to this specificity for a primary aminopropyl segment for further metabolism of the monoalkylated triamines, i.e., only examples of deaminopropylation are observed. For example, the tetraamine MM-[3,3,3] shows a substantial amount of the deaminopropylation metabolite, MM-[3,3], representing 16.5% of the total drug in the cell and even some MM-[3] (0.6%), the product of deaminopropylation of MM-[3,3]. No examples of deaminobutylation are seen, e.g., N8-alkyl-[4,3], monoalkyl-[4,4] and monoalkyl-[5,4] do not give rise to such metabolites. In the case of cells treated with ME-[3,3] or MP-[3,3], both N-dealkylation and deaminopropylation are available paths of primary metabolism. The deaminopropylation metabolite, ME-[3], represented 21.3% of the total drug in the ME-[3,3] treated cells compared to only 0.5% for the N-deethylation product, [3,3]. In contrast, the N-depropylation product, [3,3] (4.5%), predominated compared to the deaminopropylation metabolite, MP-[3], in MP-[3,3] treated cells.

In cells treated with the $N^1$-monoalkylated spermidines, N1-ME-[3,4] or N1-MP-[3,4], peaks corresponding to the respective tetraamines ME-[3,4,3] (3.7% of total drug in cell) and MP-[3,4,3] (6.1% of total drug in cell) were observed in the HPLC chromatograms of the dansylated cell extract (Table 4). In the case of cells containing substantial amounts of triamine analogues with a free primary aminopropyl end (i.e., ME-[3,3], MP-[3,3], N8-ME-[4,3] and N8-MP-[4,3]), no evidence of a tetraamine elaboration metabolite was observed. Only in those cases where a free aminobutyl end was available on a spermidine, [3,4], backbone was a tetraamine metabolite produced. No such metabolite was produced from triamines with a free aminobutyl end on a longer backbone (i.e., MP-[4,4] or N10-MP-[5,4]).

Thus, it is likely that at least two of the pathways responsible for metabolic transformation involve enzymes of the polyamine metabolic cycle present in all cells. Spermine synthase is responsible for elaboration of a spermidine analogue to the corresponding N-alkylspermine by annealing an aminopropyl segment to an exposed primary aminobutyl end of the triamine. The deaminopropylation observed in L1210 cells treated with triamine and tetraamine analogues is readily explained as a consequence of action by the SSAT/PAO polyamine degradative enzymes. The possibility that the N-dealkylation step required for further metabolic transformation of bisalkylpolyamines may also involve PAO is an interesting question raised by the metabolic patterns observed.

N-Dealkylation of analogues with a hydrophobic segment shorter than N-propyl appears to occur much less efficiently in the case of N-ethyl, or not at all in the case of N-methyl. Among the reported amine oxidases, polyamine oxidase (PAO) is the only one which usually attacks at a secondary amine center, three hydrophobic methylene carbons internal to the neutral $N^1$-acetamido nitrogen terminus of $N^1$-acetylspermidine, for example. The corresponding acetamidobutyl segment of $N^8$-acetylspermidine is not recognized and, therefore, not deaminobutylated.

Conservation of Charge. In two earlier studies, it was noted that there was a conservation of charge with respect to the total tetraamine cationic picoequivalence in the cell [Bergeron et al, Cancer Res., Vol. 49, supra; and Porter et al, Cancer Res., Vol. 51, supra]. For example, if, after 24 hours of exposure to an alkylated polyamine, each of the equivalent concentrations associated with charge on the amines of both the analogues and natural polyamine is added together, the numbers are fairly constant. For example, each picoequivalent of putrescine is associated with two picoequivalents of cationic charge, each picoequivalent of spermidine or its analogues with three, and each picoequivalent of spermine with four. In order to maintain this balance of charge, the cell processes the natural polyamines, e.g., exports them as it incorporates the analogues. The maintenance of total cellular charge holds for all of the triamines examined, except the 5,5 triamines (Table 6). The implication is that the cell will not incorporate the analogue beyond a point where the charge balance is disrupted, at which time cell death may occur. In the case of the tetraamines, the conservation of charge behavior seems to hold for 24 hours, but erodes after a period of time [Bergeron et al, Cancer Res., Vol. 49, supra]. With the triamines, the conservation of charge continues even at 48 hours.

TABLE 6

SUMMATION OF INTRACELLULAR LEVELS OF ANALOGUES AND POLYAMINES ANALYZED FOR AMINE EQUIVALENCE AFTER EXPOSURE TO POLYAMINE ANALOGUES

| Polyamine Analogues | Picoequivaents of Amine $10^6$ cells (×$10^3$) | Average ± Standard Deviation |
|---|---|---|
| Control Cell | 13.21 | |
| 2 DMNSPD | 18.40 | |
| 4 DENSPD | 13.70 | |
| 5 MPNSPD | 17.71 | |
| 6 DPNSPD | 15.01 | 16.21 ± 2.22 |
| 8 DMSPD | 16.09 | |
| 9 MESPD(N1) | 16.99 | |
| 10 MESPD(N8) | 17.99 | |
| 11 DESPD | 14.05 | |
| 12 MPSPD(N1) | 18.25 | |
| 13 MPSPD(N8) | 19.59 | |
| 14 DPSPD | 15.33 | 16.90 ± 1.89 |
| 16 DMHSPD | 20.34 | |
| 17 DEHSPD | 16.92 | |
| 18 MPHSPD | 20.55 | |
| 19 DPHSPD | 15.99 | 18.45 ± 2.34 |
| 21 DM(4,5) | 20.81 | |
| 22 DE(4,5) | 14.59 | |
| 23 DP(4,5) | 15.15 | 16.85 ± 3.44 |
| 24 DM(5,5) | 15.5 | |
| 25 DE(5,5) | 9.01 | |
| 26 DP(5,5) | 13.91 | 12.81 ± 3.38 |
| All Analogues | Mean | 16.47 ± 2.08 |

The L1210 cells were treated with polyamine analogues at 500 μM, except DEHSPD (125 μM), DM(4,5) (10 μM), DE(4,5) (15 μM), DM(5,5) (75 μM) and DE(5,5) (75 μM), for 48 hours. Levels of amine aquivalence for every analogue treated cell are averages from analysis of triplicate cell samples. Values are obtained by multiplying the number of moles of spermine by four, spermidine by three, putrescine by two and analogue by three. The typical control values in nmol/miltion L1210 cells are PUT=0.260±0.059, SPD=3.354±0.361, SPM=0.658±0.119.

Acute and Chronic Toxicity of Triamines. In early studies of polyamine toxicity in laboratory animals, triamines were found less toxic than tetraamines. Spermidine was approximately one-twentieth as nephrotoxic as spermine, and putrescine was the least toxic [Tabor et al, "Pharmacology of Spermine and Spermidine. Some Effects on Animals and Bacteria," J. Pharmacol. Exp. Ther., Vol. 116, pages 139–155 (1956); and Shaw, "Some Pharmacological Properties of the Polyamine Spermine and Spermidine—a Re-appraisal," Arch. Int. Pharmacodyn. Ther., Vol. 198, pages 36–48 (1972)].

In the current study, the acute toxicity of six analogues and the chronic toxicity of two triamines were measured (Table 7). The value of all polyamine $LD_{50}$s are shown in both mg/kg and mmol/kg for comparison. For acute toxicities, the polyamine analogues were administered as a single i.p. injection to groups of five or six animals at each dose. The animals were scored two hours after administration of the drug. It is clear that the acute $LD_{50}$s for triamine analogues are approximately twice the acute $LD_{50}$s for the corresponding tetraamine analogues.

In the chronic toxicity regimen, mice were administered the polyamine analogue in three doses per day (t.i.d.) for six days for a total of eighteen injections per animal and observed for 10 days after the final dose for lethalities. The most active triamine DE(4,5) against L1210 cells in vitro and the spermidine analogue DE(3,4) demonstrated much less toxicity in mice than the related tetraamines DE(4,5,4), DE(5,4,5) and DE(3,4,3). In the early study of tetraamines, a preliminary investigation suggested a direct ratio relationship between the $IC_{50}$ and the chronic $LD_{50}$ values [Bergeron et al, *J. Med. Chem.*, Vol. 37, supra]. However, in the triamine systems, the 96-hour $IC_{50}$ values of DE(4,5) suggested that this triamine should be about 5 times less toxic than corresponding tetraamine analogue, DE(4,5,4), and six times less toxic than DE(5,4,5) (Table 1), but, in fact, they are about eight-fold less toxic than the DE(4,5,4) and greater than ten-fold less toxic than DE(5,4,5) (Table 7). A similar difference is also observed in the chronic toxicity of DE(3,4). The ratio of the triamine to the tetraamine 96-hour $IC_{50}$s suggests that DE(3,4) should be approximately four times less toxic than DE(3,4,3), but, in fact, DE(3,4) is about five times less toxic than DE(3,4,3) in vivo. These results suggest a potential widening of the therapeutic window, which renders the triamine analogues as promising antineoplastics of lower toxicity and encourages further pursuit of animal studies.

raamine and triamine analogues, except for DENSPD and DE(4,5), reduce ODC more effectively than AdoMetDC activity, and tetraamines are more active at this. It was demonstrated that triamine analogue dealkylation was very specific for triamines with backbones of less than or equal to four methylenes and most effective for triamines and tetraamines with $N^\alpha,N^\omega$-dipropyl substituents.

Figures 9A, 9B:
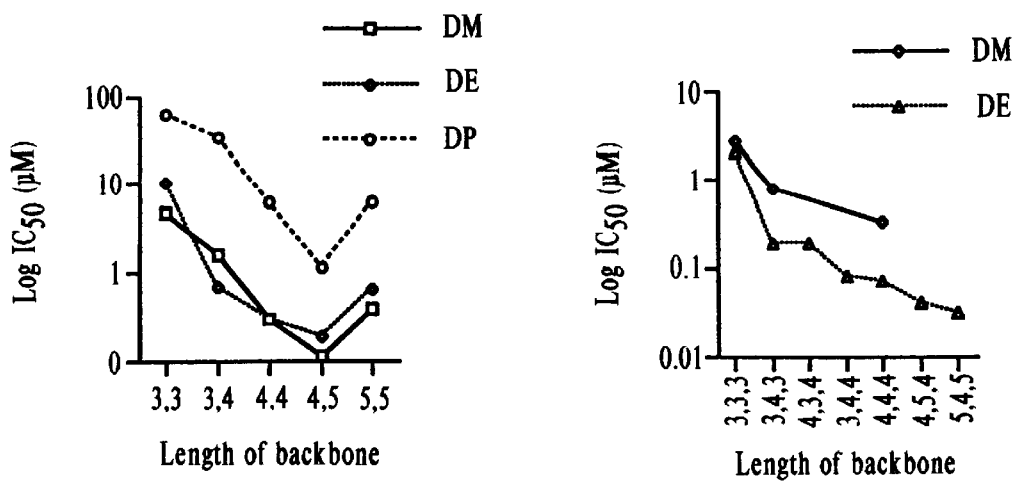
FIG. 9(a) represents the structure-activity relationship between the triamine analogues and the $IC_{50}$ values.
FIG. 9(b) illustrates the structure-activity relationship between the tetraamine analogues and the $IC_{50}$ values.

The tetraamine analogues are uniformly more active against L1210 cells than their triamine counterparts. With both the triamine and tetraamine analogues the compounds' $IC_{50}$ values are also sensitive to the size of the terminal substituent and the length of the backbone. However, the overall length between the terminal nitrogens is the most critical issue in assessing this activity; FIG. 9a illustrates the triamine case. When comparing $N^1$- with $N^8$-monoalkylspermidines, the $N^1$ compounds, both ethyl and propyl were more active than the $N^8$ compound. The fact that the $N^1$ compounds are elaborated by the cell to the corresponding and more active $N^1$-alkylspermines is in keeping with this observation. It is recalled that the $N^8$-alkylspermidines cannot be and are not further processed in the polyamine biosynthetic network. While the optimum length for the tetraamine activity has not yet been determined (FIG. 9b), evidence would suggest that the optimum length for the triamines has been determined, as seen in the terminally dialkylated (4,5)-methylene backbone series.

The triamine analogues are less toxic than the corresponding tetraamines. Furthermore, and most important when

TABLE 7

COMPARISON OF THE ACUTE AND CHRONIC TOXICITY
OF TETRAAMINE AND TRIAMINE ANALOGUES ON MICE

| TETRAAMINES | | | TRIAMINES | | |
|---|---|---|---|---|---|
| Compound | Acute[a] $LD_{50}$ mg/kg (mmol/kg) | Chronic[b] $LD_{50}$ mg/kg-day (mmol/kg.day) | Compound | Acute $LD_{50}$ mg/kg (mmol/kg) | Chronic $LD_{50}$ mg/kg-day (mmol/kg.day) |
| DE-[3,4,3] | 340(0.842) | 87[e](0.215) | DE-[3,4] | >650[d] (>3.22) | 426(1.37) |
| DE-[4,5,4] | 285(0.638) | 48(0.104) | DE-[4,5] | 555[e](1.64) | 375(1.11) |
| DE-[5,4,5] | 195(0.424) | 36(0.078) | DE-[5,5] | 500(1.42) | nd |

All of the polyamine analogues were administered in the form of hydrochloride salts.
[a]Single dose i.p.
[b]Multiple dose i.p. (t.i.d. × 6 days)
[c]At a single dose of 250 mg/kg, no death within the initial 2 hours, but all six animals were expired within seven days.
[d]15 mg/kg (t.i.d. × 3 days), 4/5 died on day 6 and 5/5 died on day 7.
[e]At a single dose of 600 mg/kg, no death within the initial 2 hours, but 5/5 died within seven days.

Figure 8:
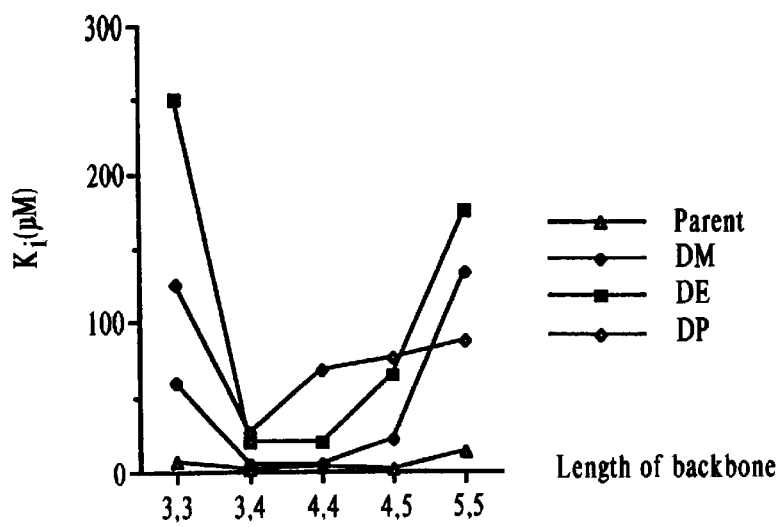
FIG. 8 depicts the structure-activity relationship between the triamine analogues and $K_i$ values.

The study serves to define the similarities and differences between triamines and tetraamine analogue antineoplastics. With both tetraamine and triamine analogues, $K_i$ values are sensitive to the size of the terminal substituents and the length of the backbone. This is illustrated for triamines in FIG. 8. Generally, the larger the terminal substituent, the more poorly the analogues are transported. In the triamine family, spermidine analogues are the best transport competitors. Interestingly, the (3,3) and (5,5) triamine analogues are most sensitive to N-terminal substituent changes. With regards to uptake, the triamines are more effectively accumulated in L1210 cells than the corresponding tetraamines. Once in the cell, tetraamine analogues have a greater impact on lowering overall polyamine pools; however, the triamines are more selective at reducing spermidine. The total intracellular charge in picoequivalents associated with polyamines, both native and analogues, is maintained by cells exposed to both tetraamines and triamines. However, cells treated with triamines are able to maintain this charge balance for a more prolonged period of time. Both tetcomparing the ratio of the 96-hour $IC_{50}$/chronic $LD_{50}$ values of the two triamines, DE(3,4) and DE(4,5), with the corresponding tetraamines, a kind of therapeutic window, the triamines appear more favorable. This is a critical issue in the choice of the best polyamine therapeutic.

The invention is illustrated by the following non-limiting examples wherein parenthetical reference numerals correspond to those in Schemes 1–5.

MENSPD (3) [Bergeron et al, *Drug Metab. Dispos.*, Vol. 23, supra] and tetraamine analogues [Bergeron et al, *J. Med. Chem.*, Vol. 31, supra; and Bergeron et al, *J. Med. Chem.*, Vol. 37, supra), except for DPNSPM and DE(5,4,5), were previously synthesized. $N^1$- and $N^8$-Acetylspermidine dihydrochlorides were purchased. N-(3-aminopropyl)-1,3-propanediamine (1) was converted to its trihydrochloride salt and recrystallized from aqueous ethanol. Sodium hydride reactions were run in distilled DMF under an inert atmosphere. THF was distilled from sodium and benzophenone. Fisher Optima grade solvents were routinely used, and organic extracts were dried with sodium sulfate. Silica gel 32-63 (40 µM "flash") was used for flash column chromatography. Melting points were determined on a Fisher-Johns melting point apparatus and are uncorrected. Proton NMR spectra were run at 90 or 300 MHz in CDCl$_3$ (not indicated) or D$_2$O with chemical shifts in parts per million downfield from tetramethylsilane or 3-(trimethylsilyl)propionic-2,2,3, 3-d$_4$ acid, sodium salt, respectively. Coupling constants (J) are in hertz. FAB mass spectra were run in a glycerol/trifluoroacetic acid matrix. Elemental analyses were also performed.

Cell culture materials, RPMI-1640 medium, fetal bovine serum, 4-(2-hydroxyethyl)-1-piperazine ethanesulfonic acid (HEPES), and 3-(N-morpholino)propanesulfonic acid (MOPS) were purchased. Cell numbers were determined by electronic particle analysis (Coulter Counter, Model ZF). The solid phase extraction columns (SPE-3 mL/500 mg) were used. Murine L1210 leukemia cells were obtained from the American Type Tissue Corporation.

[$^3$H]Spermidine for uptake determinations and acetyl coenzyme A (acetyl-1-$^{14}$C) were purchased. L-[Carboxyl-$^{14}$C]ornithine and S-adenosyl-L-[carboxyl-$^{14}$C]methionine for enzyme assays were also purchased.

Cell Culture and IC$_{50}$ Determination. Murine L1210 leukemia cells (ATCC CCL 219) were maintained in logarithmic growth in RPMI-1640 medium containing 10% fetal calf serum or a semisynthetic equivalent, NuSerum, 2% HEPES-MOPS buffer and 1 mM aminoguanidine. The IC$_{50}$s, the concentration of compound which reduces cell growth to 50% of untreated control cell growth, was determined after 48 hours and 96 hours of exposure to polyamine analogue as detailed elsewhere [Bergeron et al, *J. Med. Chem.*, Vol. 37, supra].

Polyamine Pool Analysis. L1210 cells in logarithmic growth were treated with polyamine analogue at the concentrations indicated in Table 4 for 48 hours. The cells were washed twice with cold RPMI-1640, and the pellet was treated with 0.6 N HClO$_4$ (1 ml/10$^7$ cells). Polyamine contents of the perchloric acid extracts were quantitated by HPLC of the DANSYL derivatives [Bergeron et al, *J. Med. Chem.*, Vol. 37, supra].

Uptake Determinations. The polyamine derivatives were studied for their ability to compete with [$^3$H]-SPD for uptake into L1210 cells [Bergeron et al, *J. Med. Chem.*, Vol. 37, supra]. Lineweaver-Burk plots indicated a simple competitive inhibition with respect to SPD.

Enzyme Assays. ODC and AdoMetDC activities were determined as $^{14}$CO$_2$ released from [$^{14}$C]-carboxyl-labeled L-ornithine [Seely et al, "Ornithine Decarboxylase (Mouse Kidney)," *Methods Enzymol.*, Vol. 94, pages 158–161 (1983)] or S-adenosyl-L-methionine [Pegg et al, "S-Adenosylmethionine Decarboxylase (Rat Liver)," *Methods Enzymol.*, Vol. 94, pages 234–239 (1983)], respectively. Included in each assay were untreated L1210 cells as controls, as well as cells treated with DEHSPM, a drug having a known reproducible effect on each enzyme, as positive controls.

Spermidine/spermine N$^1$-acetyltransferase activity was based on quantitation of [$^{14}$C]-N$^1$-acetylspermidine formed by acetylation of SPD with [$^{14}$C] acetyl coenzyme A according to the method of Libby et al [*Biochem. Pharmacol.*, Vol. 38, supra]. Cells treated with DENSPM were positive controls.

Toxicity in Mice. Acute and chronic toxicities were assessed in 10–12 week old CD-1 female mice from Harlan Sprague-Dawley. For acute toxicities, the polyamine analogues were administered in a single i.p. injection to groups of five or six animals at each dose. The animals were scored two hours after administration of the dose. All survivors were further observed for 10 days to assess late onset of toxicity from the single acute dose. In the chronic toxicity regimen, mice were administered polyamine analogue in three i.p. doses per day (t.i.d.) for six days, for a total of eighteen doses per animal. Appetite, weight and overall appearance were monitored daily. Animals were observed for 10 days following the final dose, at which time the final score was registered. At least three test groups of 5–6 animals each, representing three different dose levels, were evaluated for each analogue tested. These dose levels were chosen so that at least two groups presented with lethalities, one with a high fraction of lethalities (>0.50, but <1.00).

EXAMPLE 1

N$^1$,N$^4$,N$^7$-Tris(mesitylenesulfonyl)-N$^1$,N$^7$-dimethylnorspermidine (43). NaH (60% in oil, 0.44 g, 11 mmol) was added to a solution of 30 [Bergeron et al, *Drug Metab. Dispos.*, Vol. 23, supra] (3.39 g, 5 mmol) in DMF (70 mL) at 0° C. After hydrogen evolution ceased (30 minutes), iodomethane (1.63 g, 11.5 mmol) was slowly added to the mixture. After stirring for 12 hours at room temperature, the reaction mixture was quenched with distilled water (10 mL). The solvents were removed under high vacuum, and the residue was combined with H$_2$O (30 mL) and extracted with CHCl$_3$ (4×40 mL). The organic portion was washed with brine (80 mL) and evaporated by rotary evaporation. Purification by column chromatography (8:1 toluene/EtOAc) gave 2.47 g (70%) of 43 as an oil: NMR ϵ 1.73 (quintet, 4 H), 2.29 (s, 6 H), 2.54–2.55 (2 s, 18 H), 2.60 (s, 6 H), 2.99–3.06 (2 t, 8 H, J=7), 6.94 (s, 6 H). Anal. (C$_{35}$H$_{51}$N$_3$O$_6$S$_3$) C, H, N.

EXAMPLE 2

N$^1$,N$^7$-Dimethylnorspermidine Trihydrochloride (2). HBr (30% in HOAc, 30 mL) was added slowly to a mixture of 43 (2.13 g, 3.02 mmol) and phenol (12.27 g, 0.13 mol) in CH$_2$Cl$_2$ at 0° C. After stirring for 1 day at room temperature, H$_2$O (20 mL) was added to the reaction mixture followed by extraction with CH$_2$Cl$_2$ (3×30 mL). The aqueous portion was concentrated under high vacuum, and the residue was basified to pH 14 with 1 N NaOH (4 mL) and 19 N NaOH (2 mL) and extracted with CHCl$_3$ (14×10 mL). The organic extracts were concentrated, and the residue was taken up in absolute EtOH (40 mL) and acidified with concentrated HCl (2 mL). After the solvents were removed, the solid was recrystallized from aqueous EtOH to generate 0.298 g (37%) of 2 as plates: NMR (D$_2$O) δ 2.08–2.19 (m, 4 H), 2.75 (s, 6 H), 3.13–3.22 (m, 8 H). Anal. (C$_8$H$_{24}$Cl$_3$N$_3$) C, H, N.

EXAMPLE 3

N$^1$,N$^4$,N$^7$-Tris(mesitylenesulfonyl)-N$^1$,N$^7$-diethylnorspermidine (44). NaH (60%, 9.0 g, 0.23 mol), 30 [Bergeron et al, *Drug Metab. Dispos.*, Vol. 23, supra] (70.0 g, 0.103 mol), and iodoethane (19 mL, 0.24 mol) in DMF (400 mL) were reacted and worked up by the method of 43. Column chromatography (1:4 EtOAc/pet ether) afforded 63.7 g (84%) of 44 as a viscous oil: NMR δ 0.97 (t, 6 H, J=7), 1.60–1.72 (m, 4 H), 2.29 (s, 9 H), 2.54 and 2.55 (2 s, 18 H), 2.95–3.15 (m, 12 H), 6.92 (s, 6 H). Anal. (C$_{37}$H$_{55}$N$_3$O$_6$S$_3$) C, H, N. A sample was recrystallized from EtOAc/pet ether, mp 97° C.

EXAMPLE 4

$N^1,N^7$-Diethylnorspermidine Trihydrochloride (4). HBr (30% in HOAc, 300 mL), 44 (23.0 g, 30.7 mmol), and phenol (116 g, 1.23 mol) in $CH_2Cl_2$ (300 mL) were reacted, and product was isolated using the procedure of 2 to give 6.45 g (71%) of 4 as colorless plates: NMR ($D_2O$) δ 1.30 (t, 6 H, J=7), 2.05–2.18 (m, 4 H), 3.08–3.22 (m, 12 H). Anal. ($C_{10}H_{28}Cl_3N_3$) C, H, N.

EXAMPLE 5

$N^1$-Propyl-$N^1,N^4,N^7$-tris(mesitylenesulfonyl)norspermidine (45). NaH (60%, 0.52 g, 13 mmol), 30 (2.57 g, 3.8 mmol), and 1-iodopropane (0.46 mL, 4.7 mmol) in DMF were reacted and worked up by the method of 43. Column chromatography (3:1 hexane/EtOAc) afforded 1.16 g (23%) of 45 as an oil: NMR δ 0.66 (t, 3 H, J=7), 1.23–1.31 (m, 2 H), 1.58–1.62 (m, 4 H), 2.26–2.27 (2 s, 9 H), 2.51–2.52 (2 s, 12 H), 2.59 (s, 6 H), 2.82–2.99 (m, 8 H), 3.21 (t, 2 H, J=7), 4.85 (br t, 1 H), 6.89–6.92 (m, 6 H). Anal. ($C_{36}H_{53}N_3O_6S_3$) C, H, N.

EXAMPLE 6

$N^1$-Propylnorspermidine Trihydrochloride (5). HBr (30% in HOAC, 30 mL), 45 (1.14 g, 1.58 mmol), and phenol (6.4 g) in $CH_2Cl_2$ were reacted, and product was isolated using the procedure of 2 to give 87 mg (20%) of 5 as crystals: NMR ($D_2O$) δ 0.98 (t, 3 H, J=7), 1.67–1.75 (m, 2 H), 2.07–2.16 (m, 4 H), 3.01–3.21 (m, 10 H). Anal. ($C_9H_{26}Cl_3N_3$) C, H, N.

EXAMPLE 7

$N^1,N^7$-Dipropyl-$N^1,N^4,N^7$-tris(mesitylenesulfonyl)norspermidine (46). NaH (60%, 0.44 g, 11 mmol), 30 [Bergeron et al, *Drug Metab. Dispos.*, Vol. 23, supra] (3.39 g, 5 mmol), and 1-iodopropane (1.95 g, 11.5 mmol) in DMF (70 mL) were reacted and worked up by the method of 43. Column chromatography (3:1 hexane/EtOAc) afforded 3.54 g (93%) of 46 as an oil: NMR δ 0.7 (s, 6 H), 1.20–1.65 (m, 8 H), 2.25 (s, 9 H), 2.50 (s, 18 H), 2.80–3.05 (m, 12 H), 6.87 (s, 6 H). Anal. ($C_{39}H_{59}N_3O_6S_3$) C, H, N.

EXAMPLE 8

$N^1,N^7$-Dipropylnorspermidine Trihydrochloride (6). HBr (30% in HOAc, 80 mL), 46 (3.475 g, 4.57 mmol), and phenol (15.8 g) in $CH_2Cl_2$ (30 mL) were reacted, and product was isolated by the procedure of 2 to provide 1.26 g (85%) of 6 as plates: NMR ($D_2O$) δ 0.87 (t, 6 H, J=7), 1.60 (m, 4 H), 2.01 (m, 4 H), 2.93 (t, 4 H, J=7), 3.06 (m, 8 H). Anal. ($C_{12}H_{32}Cl_3N_3$) C, H, N.

EXAMPLE 9

$N^1,N^4,N^8$-Tri(mesitylenesulfonyl)spermidine (31). Mesitylenesulfonyl chloride (6.87 g, 31.4 mmol) in $CH_2Cl_2$ (30 mL) was added to spermidine trihydrochloride (2.5 g, 9.8 mmol) in 1 N NaOH (35 mL) at 0° C., and the mixture was efficiently stirred at room temperature overnight. The layers were separated, and the aqueous phase was extracted with $CHCl_3$ (3×50 mL). The organic phase was the washed with brine (100 mL), evaporated, and purified by column chromatography (4:3 hexane/EtOAc) to give 3.73 g (55%) of 31 as a white foam: NMR δ 1.30 (m, 2 H), 1.44 (m, 2 H), 1.66 (m, 2 H), 2.30 (s, 9 H), 2.46 (s, 6 H), 2.60 (s, 12 H), 2.76 (q, 2 H), 2.84 (q, 2 H), 3.04 (t, 2 H, J=7), 3.24 (t, 2 H, J=7), 4.56 (br t, 1 H), 4.92 (br t, 1 H), 6.90 (s, 2 H), 6.95 (s, 4 H). Anal. ($C_{34}H_{49}N_3O_6S_3$) C, H, N.

EXAMPLE 10

$N^1,N^8$-Dimethyl-$N^1,N^4N,N^8$-tris(mesitylenesulfonyl)spermidine (47). NaH (60%, 0.41 g, 10 mmol), 31 (2.15 g, 3.11 mmol), and iodomethane (0.62 mL, 10 mmol) in DMF (60 mL) were reacted and worked up as was 43. Column chromatography (5:3 hexane/EtOAc) furnished 2.24 g (100%) of 47 as an oil: NMR δ 1.39–1.43 (m, 4 H), 1.69–1.78 (m, 2 H), 2.28 (s, 3 H), 2.30 (s, 6 H), 2.55 (s, 12 H), 2.57 (s, 6 H), 2.60 (s, 3 H), 2.62 (s, 3 H), 2.96–3.13 (m, 8 H).

EXAMPLE 11

$N^1,N^8$-Dimethylspermidine Trihydrochloride (8). HBr (30% in HOAC, 60 mL), 47 (2.24 g, 3.11 mmol), and phenol (12.3 g) in $CH_2Cl_2$ (30 mL) were reacted, and product was isolated by the procedure of 2 to give 0.658 g (75%) of 8 as crystals: NMR ($D_2O$) δ 1.77–1.82 (m, 4 H), 2.06–2.18 (m, 2 H), 2.73 (s, 3 H), 2.75 (s, 3 H), 3.06–3.19 (m, 8 H). Anal. ($C_9H_{26}Cl_3N_3$) C, H, N.

EXAMPLE 12

$N^1,N^8$-Diethyl-$N^1,N^4,N^8$-tris(mesitylenesulfonyl)spermidine (48). NaH (80%, 0.68 g, 23 mmol), 31 (7.06 g, 10.2 mmol), and iodoethane (2.5 mL, 31 mmol) in DMF (75 mL) were combined as in 43. The mixture was heated at 65° C. for 12 hours, cooled and cautiously quenched with water (70 mL) and brine (100 mL), followed by extraction with EtOAc (5×100 mL). Combined organic extracts were washed with 100 mL of 1% $Na_2SO_3$, $H_2O$ (2×), and brine. The solvents were removed, and the residue was purified by column chromatography (4.5% EtOAc/$CH_2Cl_2$) to produce 7.21 g (94%) of 48 as an oil: NMR δ 0.8–1.8 (m, 12 H), 2.28 (s, 9 H), 2.54 (s, 18 H), 2.8–3.3 (m, 12 H), 6.90 (s, 6 H). Anal. ($C_{38}H_{57}N_3O_6S_3$) C, H, N.

EXAMPLE 13

$N^1,N^8$-Diethylspermidine Trihydrochloride (11). HBr (30% in HOAc, 150 mL), 48 (7.16 g, 9.57 mmol), and phenol (28 g, 0.30 mol) in $CH_2Cl_2$ (125 mL) were reacted, and product was isolated utilizing the procedure of 2 to give 2.17 g (73%) of 11 as white plates: NMR ($D_2O$) δ 1.28 and 1.30 (2 t, 6 H, J=7), 1.73–1.85 (m, 4 H), 2.06–2.18 (m, 2 H), 3.04–3.21 (m, 12 H). Anal. ($C_{11}H_{30}Cl_3N_3$) C, H, N.

EXAMPLE 14

$N^1,N^8$-Dipropyl-$N^1,N^4,N^8$-tris(mesitylenesulfonyl)spermidine (49). NaH (80%, 0.80 g, 27 mmol) was added to 31 (8.13 g, 11.7 mmol) in DMF (75 mL) at 0° C. The mixture was stirred at room temperature for 1 hour, and 1-iodopropane (3.5 mL, 36 mmol) was added by syringe. The mixture was stirred at 80° C. for 12 hours and worked up as was 48. Purification by column chromatography (3.5% EtOAc/$CH_2Cl_2$) resulted in 8.42 g (93%) of 49 as an oil: NMR δ 0.55–1.72 (m, 16 H), 2.25 (s, 9 H), 2.50 (s, 18 H), 2.7–3.3 (m, 12 H), 6.87 (s, 6 H). Anal. ($C_{40}H_{61}N_3O_6S_3$) C, H, N.

EXAMPLE 15

$N^1,N^8$-Dipropylspermidine Trihydrochloride (14). HBr (30% in HOAc, 150 mL), 49 (8.32 g, 10.7 mmol), and phenol (28 g, 0.29 mol) in $CH_2Cl_2$ (125 mL) were reacted, and product was isolated by the procedure of 2 to produce 2.58 g (71%) of 14 as white plates: NMR ($D_2O$) δ 0.97 and 0.98 (2 t, 6 H, J=7), 1.63–1.83 (m, 8 H), 2.06–2.19 (m, 2 H), 2.97–3.21 (m, 12 H). Anal. ($C_{13}H_{34}Cl_3N_3$) C, H, N.

EXAMPLE 16

N,N'-Bis(4-Phthalimidobutyl)mesitylenesulfonamide (37). NaH (60%, 1.6 g, 40 mmol) was added to 35 [Schreinemakers, *Recl. Trav. Chim. Pays-Bas Belg.*, Vol. 16, supra] (2.72 g, 13.5 mmol) in DMF (60 mL) at 0° C. After the mixture was stirred at 0° C. for 30 minutes, N-(4-bromobutyl)phthalimide (11.51 g, 40 mmol) in DMF (20 mL) was introduced. The mixture was stirred at room temperature for 1 hour and at 60° C. overnight. Following the workup procedure of 43, column chromatography (25:1 CHCl$_3$/acetone) gave 3.77 g (46%) of 37 as a white powder: NMR δ 1.51–1.54 (m, 8 H), 2.18 (s, 3 H), 2.57 (s, 6 H), 3.18–3.24 (m, 4 H), 3.55–3.60 (m, 4 H), 6.86 (s, 2 H), 7.69–7.25 (m, 4 H), 7.82–7.85 (m, 4 H). HRMS calcd. for $C_{33}H_{36}N_3O_6S$ 602.2325 (M+H), found. 602.2320 (M+H).

EXAMPLE 17

N,N'-Bis(4-aminobutyl)mesitylenesulfonamide (40). Hydrazine monohydrate (0.82 g, 16 mmol) was added to a suspension of 37 (3.5 g, 5.8 mmol) in absolute EtOH (100 mL), and the mixture was stirred at 65° C. for 24 hours. After cooling, the solid was filtered and washed with EtOH (2×10 mL). The combined filtrate was concentrated and purified by column chromatography (6:1 MeOH/concentrated NH$_4$OH) to produce 1.50 g (76%) of 40 as a viscous oil: NMR δ 1.37 (quintet, 4 H), 1.52 (quintet, 4 H), 2.30 (s, 3 H), 2.54 (t, 4 H, J=7), 2.58 (s, 6 H), 3.20 (t, 4 H, J=7), 7.04 (s, 3 H).

EXAMPLE 18

Homospermidine Trihydrochloride (15). HBr (30% in HOAC, 30 mL), 40 (1.50 g, 4.39 mmol) and phenol (4.49 g, 48 mmol) in CH$_2$Cl$_2$ (20 mL) were reacted, and product was isolated by the procedure of 2 to afford 0.86 g (73%) of 15 as white crystals: NMR (D$_2$O) δ 1.73–1.80 (m, 8 H), 3.03–3.14 (m, 8 H). Anal. ($C_8H_{24}Cl_3N_3$) C, H, N.

EXAMPLE 19

$N^1,N^5,N^9$-Tris(mesitylenesulfonyl)homospermidine (32). Mesitylenesulfonyl chloride (6.71 g, 30.7 mmol) and 40 (4.76 g, 14 mmol) in CH$_2$Cl$_2$ (30 mL) and 1 N NaOH (35 mL) were combined and worked up by the method of 31. Column chromatography (4:1 toluene/EtOAc) produced 3.06 g (31%) of 32 as a white foam: NMR δ 1.32–1.38 (m, 4 H), 1.44–1.54 (m, 4 H), 2.28–2.29 (2 s, 9 H), 2.54 (s, 6 H), 2.60 (s, 12 H), 2.79 (quartet, 4 H), 3.09 (t, 4 H, J=7), 4.70–4.80 (br s, 2 H), 6.90 (s, 2 H), 6.92 (s, 4 H). Anal. ($C_{35}H_{51}N_3O_6S_3$) C, H, N.

EXAMPLE 20

$N^1,N^9$-Dimethyl-$N^1,N^5,N^9$-tris(mesitylenesulfonyl) homospermidine (50). NaH (60%, 0.17 g, 4.2 mmol), 32 (1.28 g, 1.8 mmol), and iodomethane (0.25 mL, 4.0 mmol) in DMF (50 mL) were reacted and worked up as was 43. Column chromatography (2:1 toluene/EtOAc) gave 1.14 g (86%) of 50 as an oil: NMR δ 1.38–1.44 (m, 8 H), 2.28 (s, 3 H), 2.30 (s, 6 H), 2.57 (s, 18 H), 2.62 (s, 6 H), 3.03–3.14 (m, 8 H), 6.93–6.94 (2 s, 6 H). Anal. ($C_{37}H_{55}N_3O_6S_3$) C, H, N.

EXAMPLE 21

$N^1,N^9$-Dimethylhomospermidine Trihydrochloride (16). HBr (30% in HOAC, 30 mL), 50 (1.12 g, 1.52 mmol), and phenol (5.4 g, 57 mmol) in CH$_2$Cl$_2$ (25 mL) were reacted, and product was isolated by the procedure of 2 to provide 354 mg (79%) of 16 as plates: NMR (D$_2$O) δ 1.78 (m, 8 H), 2.73 (s, 6 H), 3.08–3.12 (m, 8 H). Anal. ($C_{10}H_{28}Cl_3N_3$) C, H, N.

EXAMPLE 22

$N^1,N^9$-Diethyl-$N^1,N^5,N^9$-tris(mesitylenesulfonyl) homospermidine (51). NaH (80%, 0.264 g, 8.8 mmol) was added to 35 [Schreinemakers, *Recl. Trav. Chim. Pays-Bas Belg.*, Vol. 16, supra] (0.796 g, 4 mmol) in DMF (60 mL) at 0° C. After the mixture was stirred at 0° C. for 30 minutes, 58 [Bergeron et al, *J. Med. Chem.*, Vol. 37, supra]. (3.19 g, 8.8 mmol) in DMF (15 mL) was added. The mixture was heated at 75° C. overnight and worked up by the procedure of 43. Column chromatography (3:1 hexane/EtOAc) gave 2.82 g (93%) of 51 as an oil: NMR δ 0.96 (t, 6 H), 1.20–1.40 (m, 8 H), 2.25 (s, 9 H), 2.55 (s, 18 H), 2.85–3.20 (m, 12 H), 6.90 (s, 6 H). Anal. ($C_{39}H_{59}N_3O_6S_3$) C, H, N.

EXAMPLE 23

$N^1,N^9$-Diethylhomospermidine Trihydrochloride (17). HBr (30% in HOAC, 20 mL), 51 (1.87 g, 2.45 mmol), and phenol (4.4 g, 49 mmol) in CH$_2$Cl$_2$ (20 mL) were reacted, and product was isolated by the procedure of 2 to give 493 mg (62%) of 17 as plates: NMR (D$_2$O) δ 1.30 (s, 6 H), 1.55–1.90 (m, 8 H), 2.95–3.20 (m, 12 H). Anal. ($C_{41}H_{63}N_3O_3N_3$) C, H, N.

EXAMPLE 24

$N^1,N^9$-Dipropyl-$N^1,N^5,N^9$-tris(mesitylenesulfonyl) homospermidine (52). NaH (60%, 0.17 g, 4.2 mmol), 32 (1.28 g, 1.8 mmol), and 1-iodopropane (0.39 mL, 4.0 mmol) in DMF (50 mL) were reacted and worked up using the procedure of 43. Column chromatography (4:1 hexane/EtOAc) gave 1.26 g (89%) of 52 as an oil: NMR δ 0.74 (t, 6 H, J=7), 1.26–1.45 (m, 12 H), 2.29 (s, 9 H), 2.55 (s, 18 H), 2.98–3.13 (m, 12 H), 6.87 (s, 6 H). Anal. ($C_{41}H_{63}N_3O_6S_3$) C, H, N.

EXAMPLE 25

$N^1,N^9$-Dipropylhomospermidine Trihydrochloride (19). HBr (30% in HOAc, 30 mL), 52 (1.24 g, 1.56 mmol), and phenol (5.4 g, 57 mmol) in CH$_2$Cl$_2$ (25 mL) were reacted, and product was isolated by the procedure of 2 to give 430 mg (78%) of 19 as plates: NMR (D$_2$O) δ 0.98 (t, 6 H, J=7), 1.70 (m, 4 H), 1.76–1.80 (m, 8H), 3.02 (t, 4 H, J=7), 3.08–3.12 (m, 8 H). Anal. ($C_{14}H_{36}Cl_3N_3$) C, H, N.

EXAMPLE 26

N-(3-Cyanopropyl)mesitylenesulfonamide (36). NaH (60%, 2.0 g, 50 mmol), 35 [Schreinemakers, *Recl. Trav. Chim. Pays-Bas Belg.*, Vol. 16, supra] (10.0 g, 50 mmol), and 4-bromobutyronitrile (4 mL, 40 mol) in DMF (100 mL) were combined. The mixture was heated at 80° C. overnight and worked up by the procedure of 43. Column chromatography (4:3 hexane/EtOAc) gave 5.04 g (38%) of 36 as an oil: NMR δ 1.78 (s, 3 H), 2.25 (s, 3 H), 2.35 (t, 2 H, J=7), 2.95 (q, 2 H), 5.05 (br t, 1 H), 6.90 (s, 2 H). Anal. ($C_{13}H_{18}N_2O_2S$) C, H, N.

EXAMPLE 27

N-(4-Cyanobutyl)-N-(3-cyanopropyl) mesitylenesulfonamide (38). NaH (60%, 0.90 g, 23 mmol), 36 (5.02 g, 18.85 mmol), and 5-bromovaleronitrile (2.4 mL, 21 mmol) in DMF were combined and worked up by the method of 43. Column chromatography (1:1 hexane/EtOAc) provided 5.20 g (79%) of 38 as an oil: NMR δ 1.49–1.66 (m, 4 H), 1.82 (m, 2 H), 2.22 (t, 2 H, J=7), 2.25 (t, 2 H, J=7), 2.29 (s, 3 H), 2.57 (s, 6 H), 3.19 (t, 2 H, J=7), 3.29 (t, 2 H, J=7), 6.95 (s, 2 H). Anal. ($C_{18}H_{25}N_3O_2S$) C, H, N.

EXAMPLE 28

6-(Mesitylenesulfonyl)-1,6,12-Triazadodecane (41). Raney nickel (W-2 grade, 7.60 g) and concentrated $NH_4OH$ (10 mL) were successively added to 38 (5.06 g, 14.6 mmol) in $CH_3OH$ (30 mL) and THF (30 mL) in a 200 mL Parr bottle, and a slow stream of $NH_3$ was bubbled through the mixture for 30 minutes at 0° C. After hydrogenation in a Parr bottle was carried out at 50–55 psi for 8 hours, the suspension was filtered through Celite, and the solvents were removed in vacuo to give 4.70 g (91%) of 41 as an oil: NMR δ 1.14–1.24 (m, 10 H), 2.25 (s, 3 H), 2.6 (s, 6 H), 3.05–3.25 (m, 8 H), 3.45 (s, 4 H), 6.9 (s, 2 H).

EXAMPLE 29

1,6,12-Triazadodecane Trihydrochloride (20). HBr (30% in HOAC, 33 mL), 41 (2.43 g, 6.83 mmol), and phenol (6 g, 60 mmol) in $CH_2Cl_2$ were reacted, and product was isolated by the procedure of 2 to give 0.97 g (50%) of 20 as a hygroscopic solid: NMR ($D_2O$) δ 1.47 (m, 2 H), 1.70–1.80 (m, 8 H), 3.00–3.10 (m, 8 H). Anal. ($C_9H_{26}Cl_3N_3$) C, H, N.

EXAMPLE 30

1,6,12-Tris(mesitylenesulfonyl)-1,6,12-Triazadodecane (33). Mesitylenesulfonyl chloride (4.29 g, 19.6 mmol) and 41 (3.17 g, 8.92 mmol) in $CH_2Cl_2$ (40 mL) and 1 N NaOH (20 mL) were combined and worked up by the method of 31. Column chromatography (4:3 hexane/EtOAc) generated 5.66 g (88%) of 33 as an oil: NMR δ 1.12–1.17 (m, 2 H), 1.34–1.51 (m, 8 H), 2.29 (s, 3 H), 2.30 (s, 6 H), 2.55 (s, 6 H), 2.60–2.62 (2 s, 12 H), 2.77–2.81 (m, 4 H), 3.06 (t, 2 H, J=7), 3.11 (t, 2 H, J=7), 4.50–4.60 (m, 2 H), 6.92 (s, 2 H), 6.95 (s, 2 H). Anal. ($C_{36}H_{53}N_3O_6S_3$) C, H, N.

EXAMPLE 31

2,7,13-Tris(mesitylenesulfonyl)-2,7,13-Triazapentadecane (53). NaH (60%, 0.28 g, 6.9 mmol), 33 (2.16 g, 3.0 mmol), and iodomethane (6.1 mL, 9.8 mmol) in DMF (30 mL) were combined and worked up by the method of 43. Column chromatography (7:3 hexane/EtOAc) gave 1.90 g (85%) of 53 as an oil: NMR δ 1.08–1.16 (m, 2 H), 1.38–1.50 (m, 8 H ), 2.28–2.29 (2 s, 9 H), 2.57–2.58 (2 s, 18 H), 2.63 (s, 3 H), 2.65 (s, 3 H), 3.02–3.14 (m, 8 H), 6.95 (s, 6 H); HRMS calcd. for $C_{38}H_{58}N_3O_6S_3$ 748.3487 (M+H), found. 748.3483 (M+H).

EXAMPLE 32

2,7,13-Triazatetradecane Trihydrochloride (21). HBr (30% in HOAC, 45 mL), 53 (1.85 g, 2.47 mmol), and phenol (8.5 g) in $CHCl_2$ (20 mL) were reacted, and product was isolated by the procedure of 2 to give 529 mg (69%) of 21 as crystals: NMR ($D_2O$) δ 1.42–1.52 (m, 2 H), 1.69–1.81 (m, 8 H), 2.73–2.74 (2 s, 6 H), 3.03–3.12 (m, 8 H). Anal. ($C_{11}H_{30}Cl_3N_3$) C, H, N.

EXAMPLE 33

4,9,15-Tris(mesitylenesulfonyl)-4,9,15-Triazaheptadecane (54). NaH (60%, 0.273 g, 6.84 mmol), 33 (2.24 g, 3.11 mmol), and 1-iodopropane (0.67 mL, 6.9 mmol) in DMF (30 mL) were combined and worked up by the method of 43. Column chromatography (3:1 hexane/EtOAc) provided 2.01 g (80%) of 54 as an oil: NMR δ 0.71–0.78 (m, 6 H), 1.01–1.11 (m, 2 H), 1.34–1.48 (m, 12 H), 2.29 (s, 6 H), 2.57–2.58 (2 s, 18 H), 2.98–3.13 (m, 12 H), 6.92 (s, 6 H). Anal. ($C_{42}H_{65}N_3O_6S_3.H_2O$) C, H, N.

EXAMPLE 34

4,9,15-Triazaoctadecane Trihydrochloride (23). HBr (30% in HOAC, 45 mL), 48 (1.99 g, 2.47 mmol), and phenol (8.5 g) in $CH_2Cl_2$ (20 mL) were reacted, and product was isolated by the procedure of 2 to give 852 mg (83%) of 23 as plates: NMR ($D_2O$) δ 0.97 (s, 6 H), 1.40–1.51 (m, 2 H), 1.66–1.80 (m, 12 H), 2.98–3.15 (m, 12 H). Anal. ($C_{15}H_{38}Cl_3N_3$) C, H, N.

EXAMPLE 35

N,N-Bis(4-cyanobutyl)mesitylenesulfonamide (39). NaH (80%, 1.22 g, 51 mmol), 35 [Schreinemakers, *Recl. Trav. Chim. Pays-Bas Belg.*, Vol. 16, supra) (5.0 g, 25 mmol), and 5-chlorovaleronitrile (6.5 g, 55 mmol) in DMF (50 mL) were combined. The mixture was heated at 60° C. overnight and worked up by the procedure of 43. Column chromatography (7:3 hexane/EtOAc) yielded 6.31 g (70%) of 39 as an oil: NMR δ 1.57 (m, 4 H), 1.66 (m, 4 H), 2.26 (t, 4 H, J=7), 2.60 (s, 6 H), 3.22 (t, 4 H, J=7), 6.98 (s, 2 H). Anal. ($C_{19}H_{27}N_3O_2S$) C, H, N.

EXAMPLE 36

7-Mesitylenesulfonyl-1,7,13-triazatridecane (42). Raney nickel (W-2 grade, 2.9 g) and 39 (5.69 g, 15.8 mmol) in concentrated $NH_4OH$ (10 mL) and $CH_3OH$ (60 mL) were saturated with $NH_3$ as 41. The mixture was shaken with hydrogen at 50–55 psi in a 200 mL Parr bottle for 42 hours. The suspension was filtered through Celite, and the solvents were removed in vacuo. The residue was passed through a short silica gel column (EtOH then 5% concentrated $NH_4OH$/EtOH) to give 5.71 g (98%) of 42 as a light yellow oil: NMR δ 1.17 (m, 4 H), 1.47 (m, 8 H), 2.27 (s, 3 H), 2.57 (s, 6 H), 2.61 (m, 4 H), 3.13 (t, J=7.5, 4 H), 6.91 (s, 2 H); HRMS calcd. for $C_{19}H_{36}N_3O_2S$ 370.2528 (M+H), found. 370.2530 (M+H).

EXAMPLE 37

1,7,13-Triazatridecane Trihydrochloride (24). HBr (30% in HOAc, 26 mL), 42 (2.0 g, 5.42 mmol), and phenol (4.8 g, 51 mmol) in $CHCl_3$ (40 mL) were reacted, and product was isolated by the method of 2 to give 0.97 (61%) of 24 as a white solid: NMR ($D_2O$) δ 1.45 (m, 4 H), 1.70 (m, 8 H), 3.01 (m, 8 H). Anal. ($C_{10}H_{28}Cl_3N_3$) C, H, N.

EXAMPLE 38

1,7,13-Tris(mesitylenesulfonyl)-1,7,13-triazatridecane (34). Mesitylenesulfonyl chloride (4.52 g, 20.7 mmol) and 42 (3.47 g, 9.4 mmol) in $CH_2Cl_2$ and 1 N NaOH (30 mL) were combined and worked up by the method of 31. Column chromatography (3:2 hexane/EtOAc) gave 6.44 g (93%) of 34 as a white solid: NMR δ 1.16 (m, 4 H), 1.39 (m, 8 H), 2.30 (s, 3 H), 2.31 (s, 6 H), 2.57 (s, 6 H), 2.62 (s, 12 H), 2.81 (d of t, 4 H), 3.10 (t, 4 H, J=7), 4.49 (br t, 2 H), 6.95 (s, 2 H), 6.97 (s, 4 H); HRMS calcd. for $C_{37}H_{56}N_3O_6S_3$ 734.3331 (M+H), found. 734.3351 (M+H).

EXAMPLE 39

2,8,14-Tris(mesitylenesulfonyl)-2,8,14-triazapentadecane (55). NaH (80%, 0.207 g, 6.9 mmol), 34 (1.58 g, 2.16 mmol), and iodomethane (0.30 mL, 4.8 mmol) in DMF (30 mL) were reacted and worked up as was 43. Column chromatography (5:2 hexane/EtOAc) gave 1.51 g (92%) of 55 as an oil: NMR δ 1.06–1.18 (m, 4 H), 1.40–1.52 (m, 8 H), 2.29 (s, 9 H), 2.59 (s, 18 H), 2.66 (s, 6 H), 3.03–3.14 (m, 8 H), 6.95 (s, 6 H). Anal. ($C_{39}H_{59}N_3O_6S_3$) C, H, N.

EXAMPLE 40

2,8,14-Triazapentadecane Trihydrochloride (25). HBr (30% in HOAc, 30 mL), 55 (1.48 g, 1.94 mmol), and phenol (5.2 g, 55 mmol) in $CH_2Cl_2$ (30 mL) were reacted, and product was isolated by the method of 2 to produce 480 mg (76%) of 25 as needles: NMR ($D_2O$) δ 1.4–1.5 (quintet, 4 H), 1.7–1.8 (quintet, 8 H), 2.7 (s, 6 H), 3.05 (t, 8 H, J=7). Anal. ($C_{12}H_{32}Cl_3N_3$) C, H, N.

EXAMPLE 41

3,9,15-Tris(mesitylenesulfonyl)-3,9,15-triazaheptadecane (56). NaH (80%, 0.52 g, 17 mmol), 34 (3.2 g, 4.36 mmol), and iodoethane (1.5 g, 9.6 mmol) in DMF (20 mL) were reacted and worked up by the method of 43. Column chromatography (4:1 hexane/EtOAc) gave 2.91 g (85%) of 56 as a white solid: mp 60–62° C.; NMR δ 1.01 (t, 6 H, J=7), 1.08 (m, 4 H), 1.42 (m, 8 H), 2.29 (s, 9 H), 2.57 (s, 6 H), 2.58 (s, 12 H), 3.07 (t, 4 H, J=7), 3.11 (t, 4 H, J=7), 3.17 (q, 4 H), 6.92 (s, 6 H). Anal. ($C_{41}H_{63}N_3O_6S_3$) C, H, N.

EXAMPLE 42

3,9,15-Triazaheptadecane Trihydrochloride (26). HBr (30% in HOAc, 20 mL), 56 (2.9 g, 3.67 mmol), and phenol (3.25 g, 34.5 mmol) in $CHCl_3$ (27 mL) were reacted, and product was isolated by the method of 2 to give 1.0 g (77%) of 26 as white crystals: NMR ($D_2O$) δ 1.28 (t, 6 H, J=7), 1.45 (m, 4 H), 1.73 (m, 8 H), 3.08 (m, 12 H). Anal. ($C_{14}H_{36}Cl_3N_3$) C, H, N.

EXAMPLE 43

4,10,16-Tris(mesitylenesulfonyl)-4,10,16-triazanonadecane (57). NaH (80%, 198 mg, 6.6 mmol), 34 (1.51 g, 2.06 mmol), and 1-iodopropane (0.44 mL, 4.5 mmol) in DMF (40 mL) were reacted and worked up by the method of 43. Column chromatography (7:2/hexane/EtOAc) provided 1.61 g (95%) of 57 as an oil: NMR δ 0.75 (t, 6 H, J=7), 1.02–1.14 (m, 4 H), 1.36–1.52 (m, 12 H), 2.30 (s, 9 H), 2.60 (s, 18 H), 3.02–3.16 (m, 12 H), 6.95 (s, 6 H). Anal. ($C_{43}H_{67}N_3O_6S_3$) C, H, N.

EXAMPLE 44

4,10,16-Triazanonadecane Trihydrochloride (27). HBr (30% in HOAC, 30 mL), 57 (1.58 g, 1.93 mmol), and phenol (5.2 g, 55 mmol) were reacted, and product was isolated by the method of 2 to give 579 mg (79%) of 27 as plates: NMR ($D_2O$) δ 0.95 (t, 6 H, J=7), 1.38–1.49 (m, 4 H), 1.62–1.77 (m, 12 H), 2.95–3.05 (m, 12 H). Anal. ($C_{16}H_{40}Cl_3N_3$) C, H, N.

EXAMPLE 45

N-(5-Bromopentyl)-N-ethylmesitylenesulfonamide (61). NaH (80%, 1.26 g, 42 mmol), 60 [Schreinemakers, *Recl. Trav. Chim. Pays-Bas Belg.*, Vol. 16, supra] (6.82 g, 30.0 mmol), and 1,5-dibromopentane (49 mL, 0.36 mol) in DMF (100 mL) were combined. The mixture was heated at 74° C. overnight and worked up by the procedure of 43. Column chromatography (7:1 hexane/EtOAc) produced 7.87 g (70%) of 61 as an oil: NMR δ 1.00 (t, 3 H, J=7), 1.30–1.75 (m, 6 H), 2.20 (s, 3 H), 2.50 (s, 6 H), 3.02–3.30 (m, 6 H), 6.80 (s, 2 H); HRMS calcd. for $C_{16}H_{27}BrNO_2S$ 376.0946 (M+H), found. 376.0960 (M+H).

EXAMPLE 46

$N^1,N^4$-Bis(mesitylenesulfonyl)-$N^1$-(tert-butoxycarbonyl)-$N^4$-ethyl-1,4-diaminobutane (62). NaH (80%, 0.45 g, 23 mmol) was added to 59 (Bergeron et al, *J. Med. Chem.*, Vol. 37, supra]. (3.45 g, 11.5 mmol) in DMF (100 mL) at 0° C. After the mixture was stirred at 0° C. for 40 minutes, 58 [Bergeron et al, *J. Med. Chem.*, Vol. 37, supra]. (5.00 g, 13.8 mmol) in DMF (10 mL) was added. The mixture was heated at 60° C. for 18 hours and then worked up by the method of 43. Column chromatography with (20:1 toluene/EtOAc) gave 6.44 g (96%) of 62 as an oil: NMR δ 1.12 (t, 3 H, J=7), 1.20 (s, 9 H), 1.55–1.65 (m, 4 H), 2.29 (s, 2 H), 2.30 (s, 2 H), 2.52 (s, 4 H), 2.62 (s, 4 H), 3.16–3.24 (m, 2 H), 3.30 (q, 2 H), 3.70 (m, 2 H), 6.94 (s, 4 H).

EXAMPLE 47

$N^1,N^4$-Bis(mesitylenesulfonyl)-N-ethyl-1,4-diaminobutane (63). TFA (70 mL) was slowly dripped into a solution of 62 (6.20 g, 10.6 mmol) in $CH_2Cl_2$ (30 mL) at 0° C. After the solution was stirred at 0° C. for 20 minutes and at room temperature for 30 minutes, solvents were removed by rotary evaporation. The residue was basified to pH >8 with saturated $NaHCO_3$ and extracted with $CH_2Cl_2$ (4×100 mL). Removal of organic extracts led to 5.10 g (100%) of 63 as a foam: NMR δ 0.97 (t, 3 H, J=7), 1.20–1.50 (m, 4 H), 2.25 (s, 6 H), 2.50–2.55 (2 s, 12 H), 2.95–3.25 (m, 6 H), 4.45 (t, 1 H), 6.85 (s, 4 H). Anal. ($C_{24}H_{36}N_2O_4S_2$) C, H, N.

EXAMPLE 48

3,8,14-Tris(mesitylenesulfonyl)-3,8,14-Triazahexadecane (64). NaH (80%, 0.41 g, 14 mmol) was added to 63 (5.10 g, 10.6 mmol) in DMF (50 mL) at 0° C. After the mixture was stirred at 0° C. for 30 minutes, 61 (4.80 g, 12.7 mmol) in DMF (10 mL) was added. The mixture was heated at 89° C. overnight and then worked up by the method of 43. Column chromatography (12:1 toluene/EtOAc) gave 5.43 g (66%) of 64 as an oil: NMR δ 0.9–1.1 (m, 6 H), 1.2–1.5 (m, 10 H), 2.25 (s, 6 H), 2.30 (s, 3 H), 2.55 (s, 18 H), 2.9–3.2 (m, 12 H), 6.85 (s, 6 H). Anal. ($C_{40}H_{61}N_3O6S_3$) C, H, N.

EXAMPLE 49

3,8,14-Triazahexadecane Trihydrochloride (22). HBr (30% in HOAc, 100 mL), 64 (5.4 g, 7.0 mmol), and phenol (25 g, 0.28 mol) were reacted, and product was isolated by the method of 2 to give 1.63 g (69%) of 22 as plates: NMR ($D_2O$) δ 1.38 (t, 3 H, J=7), 1.39 (t, 3 H, J=7), 1.60–1.70 (m, 10 H), 3.02–3.15 (m, 12 H). Anal. ($C_{13}H_{34}Cl_3N_3$) C, H, N.

EXAMPLE 50

N$^1$-Triphenylmethyl-1,3-diaminopropane (68). A solution of triphenylmethyl chloride (6.97 g, 25 mmol) in CH$_2$Cl$_2$ (100 mL) was added dropwise to a rapidly stirred solution of 1,3-diaminopropane (9.86 g, 133 mmol) in CH$_2$Cl$_2$ (100 mL). After stirring at room temperature for 2 days, 1 N NaOH (50 mL) was added to the mixture, which was extracted with CHCl$_3$ (3×50 mL). Organic extracts were washed with 100 mL of H$_2$O and brine. After solvent removal, column chromatography (3% concentrated NH$_4$OH/MeOH) gave 6.32 g (80%) of 68 as a white solid: mp 59–61° C. [Parg et al, "A Semiconducting Langmuir-Blodgett Film of a Non-amphiphilic Bis-tetrathiofulvalene Derivative," *J. Mater. Chem.*, Vol. 5, pages 1609–1615 (1995); mp 59–61° C.]; NMR δ 1.35–1.65 (m, 6 H), 2.18 (t, 2 H, J=7), 2.77 (s, 1 H), 7.13–7.24 (m, 9 H), 7.44–7.46 (m, 6 H). Anal. (C$_{22}$H$_{24}$N$_2$) C, H, N.

EXAMPLE 51

N$^1$-Mesitylenesulfonyl-N$^3$-triphenylmethyl-1,3-diaminopropane (70). Mesitylenesulfonyl chloride (5.25 g, 24 mmol) and 68 (6.30 g, 20 mmol) in CH$_2$Cl$_2$ (30 mL) and 1 N NaOH (27 mL) were combined and worked up by the method of 31. Column chromatography (7:2 hexane/EtOAc) gave 8.37 g (84%) of 70 as a white solid: NMR δ 1.56–1.66 (m, 3 H), 2.17 (t, 2 H, J=7), 2.29 (s, 3 H), 2.60 (s, 6 H), 3.08 (q, 2 H), 5.25 (br t, 1 H), 6.93 (s, 2 H), 7.15–7.28 (m, 9 H), 7.35–7.39 (m, 6 H). Anal. (C$_{31}$H$_{34}$N$_2$O$_2$S) C, H, N.

EXAMPLE 52

N$^1$-Triphenylmethyl-1,4-diaminobutane (69). A solution of triphenylmethyl chloride (59.94 g, 0.215) in CH$_2$Cl$_2$ (500 mL) was added dropwise to a rapidly stirred solution of 1,4-diaminobutane (96.47 g, 1.094 mol) in CH$_2$Cl$_2$ (1.1 L) over a period of 2 hours. The reaction mixture was stirred at room temperature for 3 days and was worked up following the method of 68 to give a quantitative yield of 69 as an oil which was used directly in the next step: NMR δ 1.39–1.54 (m, 7 H), 2.12 (t, 2 H, J=7), 2.62 (t, 2 H, J=7), 7.13–7.28 (m, 9 H), 7.41–7.47 (m, 6 H).

EXAMPLE 53

N$^1$-Mesitylenesulfonyl-N$^4$-triphenylmethyl-1,4-diaminobutane (71). Mesitylenesulfonyl chloride (3.1 g, 14 mmol) and 69 (3.39 g, 10.3 mmol) in CH$_2$Cl$_2$ (20 mL) and 1 N NaOH (15 mL) were combined and worked up by the method of 31. Column chromatography (1:3 hexane/EtOAc) furnished 3.79 g (72%) of 71 as a white solid: NMR δ 1.41–1.50 (m, 5 H), 2.03–2.08 (t, 2 H, J=7), 2.27 (s, 3 H), 2.62 (s, 6 H), 2.87 (q, 2 H), 4.41 (br t, 1 H), 6.93 (s, 2 H), 7.15–7.28 (m, 9 H), 7.40–7.44 (m, 6 H). Anal. (C$_{32}$H$_{36}$N$_2$O$_2$S) C, H, N.

EXAMPLE 54

N-Propylmesitylenesulfonamide (65). Mesitylenesulfonyl chloride (12.0 g, 55 mmol) and propylamine (2.96 g, 50 mmol) in CH$_2$Cl$_2$ (60 mL) and 1 N NaOH (60 mL) were combined and worked up by the method of 31. Column chromatography (3:1 hexane/EtOAc) afforded 8.44 g (85%) of 65 as a crystalline solid: mp 53–54° C.; NMR δ 0.86 (t, 3 H, J=7), 1.44–1.51 (m, 2 H), 2.30 (s, 3 H), 2.64 (s, 6 H), 2.86 (q, 2 H), 4.40 (br t, 1 H), 6.96 (s, 2 H). Anal. (C$_{12}$H$_{19}$NO$_2$S) C, H, N.

EXAMPLE 55

N-(3-Bromopropyl)-N-propylmesitylenesulfonamide (66). NaH (60%, 0.34 g, 8.4 mmol), 65 (1.7 g, 7.0 mmol), and 1,3-dibromopropane (17.0 g, 84 mmol) in DMF (30 mL) were combined and worked up by the method of 43. Column chromatography (6:1 hexane/EtOAc) produced 1.82 g (80%) of 66 as an oil: NMR δ 0.79 (s, 3 H), 1.48–1.56 (m, 2 H), 2.04–2.10 (m, 2 H), 2.30 (s, 3 H), 2.60 (s, 6 H), 3.09–3.14 (m, 2 H), 3.29–3.36 (m, 4 H). Anal. (C$_{15}$H$_{24}$BrNO$_2$S) C, H, N.

EXAMPLE 56

N-(4-Bromobutyl)-N-propylmesitylenesulfonamide (67). NaH (60%, 0.70 g, 17 mmol), 65 (3.5 g, 14.5 mmol), and 1,4-dibromobutane (37.6 g, 174 mmol) in DMF (40 mL) were combined and worked up by the method of 43. Excess 1,4-dibromobutane was removed by a Kugelrohr apparatus under high vacuum. Column chromatography (7:1 hexane/EtOAc) produced 5.21 g (95%) of 67 as an oil: NMR δ 0.79 (t, 3 H, J=7), 1.46–1.54 (m, 2 H), 1.64–1.78 (m, 4 H), 2.30 (s, 3 H), 2.60 (s, 6 H), 3.11 (t, 2 H, J=7), 3.21 (t, 2 H, J=7), 3.31 (t, 2 H, J=7), 6.93 (s, 2 H). Anal. (C$_{16}$H$_{26}$BrNO$_2$S) C, H, N.

EXAMPLE 57

6,10-Bis(mesitylenesulfonyl)-1-triphenylmethyl-1,6,10-triazatridecane (72). NaH (60%, 0.24 g, 5.96 mmol) was added to 71 (2.55 g, 4.97 mmol) in DMF (40 mL) at 0° C. After the mixture was stirred at 0° C. for 20 minutes, 66 (1.80 g, 4.97 mmol) in DMF (20 mL) was added. The mixture was stirred at room temperature for 1 day and then worked up following the method of 43. Column chromatography (20:1 toluene/EtOAc) produced 3.72 g (94%) of 72 as an oil: NMR δ 0.73 (t, 3 H, J=7), 1.26–1.70 (m, 8 H), 2.01 (t, 2 H, J=7), 2.26 (s, 3 H), 2.27 (s, 3 H), 2.54 (s, 12 H), 2.96–3.04 (m, 8 H), 6.90 (s, 4 H), 7.18–7.45 (m, 15 H). Anal. (C$_{47}$H$_{59}$N$_3$O$_4$S$_2$) C, H, N.

EXAMPLE 58

5,10-Bis(mesitylenesulfonyl)-1-triphenylmethyl-1,5,10-triazatridecane (73). NaH (60%, 0.22 g, 5.42 mmol), 70 (2.25 g, 4.52 mmol) in DMF (40 mL), and 67 (1.70 g, 4.52 mmol) in DMF (20 mL) were reacted and worked up following the method of 72. Column chromatography (25:1 toluene/EtOAc) produced 2.87 g (80%) of 73 as an oil: NMR δ 0.75 (t, 3 H, J=7), 1.41–1.46 (m, 9 H), 1.97 (t, 2 H, J=7), 2.26 (s, 6 H), 2.53 (s, 6 H), 2.56 (s, 6 H), 3.04 (t, 2 H, J=7), 3.10–3.15 (m, 6 H), 6.88 (s, 2 H), 6.90 (s, 2 H), 7.15–7.38 (m, 15 H). Anal. (C$_{47}$H$_{59}$N$_3$O$_4$S$_2$) C, H, N.

EXAMPLE 59

6,11-Bis(mesitylenesulfonyl)-1-triphenylmethyl-1,6,11-triazatetradecane (74). NaH (60%, 0.12 g, 2.90 mmol), 71 (1.24 g, 2.42 mmol) in DMF (30 mL), and 67 (0.91 g, 2.42 mmol) in DMF (10 mL) were reacted and worked up following the method of 72. Column chromatography (25:1 toluene/EtOAc) gave 1.67 g (85%) of 74 as an oil: NMR δ 0.74 (t, 3 H, J=7), 1.35–1.45 (m, 11 H), 2.00 (t, 2 H, J=7), 2.25 (s, 3 H), 2.28 (s, 3 H), 2.55 (s, 6 H), 2.56 (s, 6 H), 2.98–3.08 (m, 8 H), 6.90 (s, 2 H), 6.91 (s, 2 H), 7.15–7.44 (m, 15 H). Anal. (C$_{48}$H$_{61}$N$_3$O$_4$S$_2$) C, H, N.

EXAMPLE 60

$N^2$-Propylspermidine Trihydrochloride (12). HBr (30% in HOAC, 45 mL), 72 (3.70 g, 4.66 mmol), and phenol (8.4 g, 89 mmol) in $CH_2Cl_2$ (50 mL) were reacted, and product was isolated by the method of 2 to give 1.02 g (74%) of 12 as plates: NMR ($D_2O$) δ 0.98 (t, 3 H, J=7), 1.66–1.79 (m, 6 H), 2.06–2.17 (m, 2 H), 3.01–3.19 (m, 10 H). Anal. ($C_{10}H_{28}Cl_3N_3$) C, H, N.

EXAMPLE 61

$N^8$-Propylspermidine Trihydrochloride (13). HBr (30% in HOAc, 35 mL), 73 (2.85 g, 3.59 mmol), and phenol (6.5 g, 69 mmol) in $CH_2Cl_2$ (30 mL) were reacted, and product was isolated by the method of 2 to give 810 mg (76%) of 13 as plates: NMR ($D_2O$) δ 0.98 (t, 3 H, J=7), 1.66–1.79 (m, 6 H), 2.01–2.12 (m, 2 H), 2.99–3.14 (m, 10 H). Anal. ($C_{10}H_{28}Cl_3N_3$) C, H, N.

EXAMPLE 62

$N^1$-Propylhomospermidine Trihydrochloride (18). HBr (30% in HOAc, 20 mL), 74 (1.65 g, 2.0 mmol), and phenol (3.6 g, 38 mmol) in $CH_2Cl_2$ (20 mL) were reacted, and product was isolated by the method of 2 to give 268 mg (43%) of 18 as plates: NMR ($D_2O$) δ 0.98 (t, 3 H, J=7), 1.66–1.80 (m, 10 H), 2.99–3.11 (m, 10 H). HRMS calcd. for $C_{11}H_{28}N_3$ 202.2283 (free amine, M+H), found. 202.2296 (M+H).

EXAMPLE 63

$N^1$-Ethylspermidine Trihydrochloride (9). Lithium aluminum hydride (1.6 g, 42 mmol) was added to $N^1$-acetylspermidine dihydrochloride (0.50 g, 1.9 mmol) in THF (300 mL) at 0° C., and the mixture was heated at reflux for 17 hours. The reaction was quenched at 0° C. with $H_2O$ (1.6 mL), 15% NaOH (1.6 mL), and $H_2O$ (4.8 mL). Salts were filtered and washed with THF, and solvent was removed by rotary evaporation. The residue was distilled in a Kugelrohr apparatus under high vacuum (T≦60° C.), and the distillate was dissolved in EtOH (5 mL) and treated with concentrated HCl (0.5 mL). Recrystallization from aqueous EtOH gave 0.096 g (18%) of 9 as crystals: NMR ($D_2O$) δ 1.30 (t, 3 H, J=7), 1.72–1.83 (m, 4 H), 2.05–2.16 (m, 2 H), 3.02–3.19 (m, 10 H). Anal. ($C_9H_{26}Cl_3N_3$) C, H, N.

EXAMPLE 64

$N^8$-Ethylspermidine Trihydrochloride (10). Lithium aluminum hydride (1.73 g, 45.6 mmol) and $N^8$-acetylspermidine dihydrochloride (0.54 g, 2.1 mmol) in THF (300 mL) were reacted, and product was isolated by the method of 9 to furnish 0.164 g (28%) of 10 as crystals: NMR ($D_2O$) δ 1.29 (t, 3 H, J=7), 1.73–1.83 (m, 4 H), 2.03–2.16 (m, 2 H), 3.05–3.20 (m, 10 H). Anal. ($C_9H_{26}Cl_3N_3$) C, H, N.

EXAMPLE 65

$N^1,N^4,N^8,N^{11}$-Tetrakis(mesitylenesulfonyl)-$N^1,N^{11}$-dipropylnorspermine (76). NaH (60%, 3.60 g, 90.0 mmol), 75 [Bergeron et al, *J. Med. Chem.*, Vol. 37, supra]. (27.5 g, 30.0 mmol), and 1-iodopropane (7.5 mL, 77 mmol) in DMF (200 mL) were combined, and the reaction was worked up by the method of 48. Column chromatography (5:1 toluene/EtOAc) resulted in 27.79 g (92%) of 76 as a white foam: NMR δ 0.72 (t, 6 H, J=7), 1.2–1.7 (m, 10 H), 2.30 (s, 12 H), 2.55 (s, 24 H), 2.92–3.03 (m, 16 H), 6.93 (s, 8 H). Anal. ($C_{51}H_{76}N_4O_8S_4$) C, H, N.

EXAMPLE 66

$N^1,N^{11}$-Dipropylnorspermine Tetrahydrochloride (28). HBr (30% in HOAc, 500 mL), 76 (27.54 g, 27.5 mmol), and phenol (105 g, 1.12 mol) in $CH_2Cl_2$ (250 mL) were reacted, and product was isolated by the method of 2 to give 7.82 g (68%) of 28 as white plates: NMR ($D_2O$) δ 0.98 (t, 6 H, J=7), 1.64–1.78 (m, 4 H), 2.07–2.21 (m, 6 H), 3.00–3.25 (m, 16 H). Anal. ($C_{15}H_{40}Cl_4N_4$) C, H, N.

EXAMPLE 67

N-(5-Chloropentyl)-N-ethylmesitylenesulfonamide (77). NaH (80%, 1.34 g, 44.7 mmol) was added to 60 [Bergeron et al, *J. Med. Chem.*, Vol. 37, supra]. (7.68 g, 33.8 mmol) in DMF (130 mL) at 0° C. The mixture was stirred at room temperature for 1 hour, and cooled to 0° C. 1,5-Dichloropentane (45 mL, 0.35 mol) was added all at once. The reaction was stirred at 55° C. for 12 hours and was worked up by the method of 48. Column chromatography (11.5% EtOAc/hexane) gave 10.54 g (94%) of 77 as an oil: NMR δ 1.07 (t, 3 H, J=8), 1.25–1.37 (m, 2 H), 1.47–1.71 (m, 4 H), 2.30 (s, 3 H), 2.60 (s, 6 H), 3.14–3.28 (m, 4 H), 3.44 (t, 2 H, J=7), 6.94 (s, 2 H). Anal. ($C_{16}H_{26}ClNO_2S$) C, H, N.

EXAMPLE 68

3,9,14,20-Tetrakis(mesitylenesulfonyl)-3,9,14,20-tetraazadocosane (79). NaH (80%, 1.14 g, 38.0 mmol) was added to 78 [Bergeron et al, *J. Med. Chem.*, Vol. 37, supra]. (5.77 g, 12.7 mmol) in DMF (75 mL) at 0° C. The mixture was stirred at room temperature for 1 hour, and 77 (10.51 g, 31.7 mmol) in DMF (55 mL) was added by cannula. The reaction was stirred at 55° C. for 16 hours and was worked up by the method of 48. Column chromatography (30% EtOAc/hexane) afforded 12.67 g (96%) of 79 as an oil: NMR δ 0.97–1.12 (m, 10 H), 1.30–1.47 (m, 12 H), 2.29 (s, 12 H), 2.56 and 2.58 (2 s, 24 H), 2.97–3.22 (m, 16 H), 6.93 (s, 8 H). Anal. ($C_{54}H_{82}N_4O_8S_4$) C, H, N.

EXAMPLE 69

3,9,14,20-Tetraazadocosane Tetrahydrochloride (29). HBr (30% in HOAc, 195 mL), 79 (12.66 g, 12.1 mmol), and phenol (33.61 g, 0.357 mol) in $CH_2Cl_2$ (135 mL) were reacted, and product was isolated by the method of 2 to provide 4.50 g (81%) of 29 as white crystals: NMR ($D_2O$) δ 1.28 (t, 6 H, J=7), 1.40–1.52 (m, 4 H), 1.66–1.80 (m, 12 H), 3.00–3.14 (m, 16 H). Anal. ($C_{18}H_{46}Cl_4N_4$).

Analytical Data

2 Anal. calcd. for $C_8H_{24}Cl_3N_3$: C, 35.77; H, 9.00; N, 15.64. Found: C, 35.91; H, 8.96; N, 15.69.

4 Anal. calcd. for $C_{10}H_{28}Cl_3N_3$: C, 40.48; H, 9.51; N, 14.16. Found: C, 40.31; H, 9.36; N, 14.12.

5 Anal. calcd. for $C_9H_{26}Cl_3N_3$: C, 38.24; H, 9.27; N, 14.87. Found: C, 38.15; H, 9.32; N, 14.75.

6 Anal. calcd. for $C_{12}H_{32}Cl_3N_3$: C, 44.38; H, 9.93; N, 12.94. Found: C, 44.42; H, 9.89; N, 12.88.

8 Anal. calcd. for $C_9H_{26}Cl_3N_3$: C, 38.24; H, 9.27; N, 14.86. Found: C, 38.19; H, 9.28; N, 14.79.

9 Anal. calcd. for $C_9H_{26}Cl_3N_3$: C, 38.24; H, 9.27; N, 14.86. Found: C, 38.31; H, 9.23; N, 14.90.

10 Anal. calcd. for $C_9H_{26}Cl_3N_3$: C, 38.24; H, 9.27 N, 14.86. Found: C, 38.28; H, 9.31; N, 14.95.

11 Anal. calcd. for $C_{11}H_{30}Cl_3N_3$: C, 42.52; H, 9.73; N, 13.52. Found: C, 42.59; H, 9.79; N, 13.47.

12 Anal. calcd. for $C_{10}H_{28}Cl_3N_3$: C, 40.48; H, 9.51; N, 14.16. Found C, 40.55; H, 9.45; N, 14.18.

13 Anal. calcd. for $C_{10}H_{28}Cl_3N_3$: C, 40.48; H, 9.51; N, 14.16. Found C, 40.52; H, 9.52; N, 14.09.

14 Anal. calcd. for $C_{13}H_{34}Cl_3N_3$: C, 46.09; H, 10.12; N, 12.40. Found: C, 46.15; H, 10.17; N, 12.43.

15 Anal. calcd. for $C_8H_{24}Cl_3N_3$: C, 35.77; H, 9.00; N, 15.64; S, 39.59. Found: C, 35.88; H, 8.91; N, 15.68; S, 39.48.

16 Anal. calcd. for $C_{10}H_{28}Cl_3N_3$: C, 40.48; H, 9.51; N, 14.16. Found: C, 40.45; H, 9.44; N, 14.09.

17 Anal. calcd. for $C_{12}H_{32}Cl_3N_3$: C, 44.38; H, 9.93; N, 12.94. Found: C, 44.49; H, 9.98; N, 12.96.

19 Anal. calcd. for $C_{14}H_{36}Cl_3N_3$: C, 47.66; H, 10.29; N, 11.91. Found: C, 47.70; H, 10.21; N, 11.86.

20 Anal. calcd. for $C_9H_{26}Cl_3N_3$: C, 38.24; H, 9.27; N, 14.87. Found: C, 38.28; H, 9.22; N, 14.82.

21 Anal. calcd. for $C_{11}H_{30}Cl_3N_3$: C, 42.52; H, 9.73; N, 13.52. Found: C, 42.52; H, 9.69; N, 13.58.

22 Anal. calcd. for $C_{13}H_{34}Cl_3N_3$: C, 46.09; H, 10.12; N, 12.40. Found: C, 46.20; H, 10.08; N. 12.47.

23 Anal. calcd. for $C_{15}H_{38}Cl_3N_3$: C, 49.11; H, 10.44; N, 11.45. Found: C, 49.02; H, 10.40; N, 11.42.

24 Anal. calcd. for $C_{10}H_{28}Cl_3N_3$: C, 40.48; H, 9.51; N, 14.16; Cl, 35.85. Found: C, 40.63; H, 9.44; N, 14.16; Cl, 35.70.

25 Anal. calcd. for $C_{12}H_{32}Cl_3N_3$: C, 44.38; H, 9.93; N, 12.94. Found: C, 44.33; H, 9.90; N, 12.89.

26 Anal. calcd. for $C_{14}H_{36}Cl_3N_3$: C, 47.66; H, 10.28; N, 11.91; Cl, 30.15. Found: C, 47.69; H, 10.24; N, 11.96; Cl, 30.08.

27 Anal. calcd. for $C_{16}H_{40}Cl_3N_3$: C, 50.46; H, 10.59; N, 11.03. Found: C, 50.49; H, 10.55; N, 11.07.

28 Anal. calcd. for $C_{15}H_{40}Cl_4N_4$: C, 43.07; H, 9.64; N, 13.39. Found: C, 43.24; H, 9.57; N, 13.44.

29 Anal. calcd. for $C_{18}H_{46}Cl_4N_4$: C, 46.96; H, 10.07; N, 12.17. Found: C, 47.08; H, 9.98; N, 12.18.

30 Anal. calcd. for $C_{33}H_{47}N_3O_6S_3$: C, 58.47; H, 6.99; N, 6.20. Found: C, 58.36; H, 6.95; N, 6.18.

31 Anal. calcd. for $C_4H_{49}N_3O_6S_3$: C, 59.02; H, 7.14; N, 6.07. Found: C, 58.74; H, 7.12; N, 5.99.

32 Anal. calcd. for $C_{35}H_{51}N_3O_6S_3$: C, 59.55; H, 7.28; N, 5.95. Found: C, 59.34; H, 7.29; N, 5.92.

33 Anal. calcd. for $C_{36}H_{53}N_3O_6S_3$: C, 60.05; H, 7.42; N, 5.84. Found: C, 59.88; H, 7.41; N, 5.80.

36 Anal. calcd. for $C_{13}H_{18}N_2O_2S$: C, 58.62; H, 6.81; N, 10.52. Found: C, 58.52; H, 6.86; N, 10.46.

38 Anal. calcd. for $C_{18}H_{25}N_3O_2S$: C, 62.22; H, 7.25; N, 12.09; S, 8.87. Found: C, 62.24; H, 7.28; N, 11.99.

39 Anal. calcd. for $C_{19}H_{27}N_3O_2S$: C, 63.13; H, 7.53; N, 11.62; S, 8.87. Found: C, 63.31; H, 7.68; N, 11.43; S, 8.97.

43 Anal. calcd. for $C_{35}H_{51}N_3O_6S_3$: C, 59.55; H, 7.28; N, 5.95. Found: C, 59.50; H, 7.33; N, 5.88.

44 Anal calcd. for $C_{37}H_{55}N_3O_6S_3$: C, 60.54; H, 7.55; N, 5.72. Found: C, 60.64; H, 7.54; N, 5.73.

45 Anal. calcd. for $C_{36}H_{53}N_3O_6S_3$: C, 60.05; H, 7.42; N, 5.84. Found: C, 59.79; H, 7.32; N, 5.70.

46 Anal. calcd. for $C_{39}H_{59}N_3O_6S_3$: C, 61.55; H, 7.68; N, 5.52. Found: C, 61.52; H, 7.79; N, 5.55.

48 Anal. calcd. for $C_{38}H_{57}N_3O_6S_3$: C, 61.01; H, 7.68; N, 5.62. Found: C, 61.22; H, 7.76; N, 5.56.

49 Anal. calcd. for $C_{40}H_{61}N_3O_6S_3$: C, 61.90; H, 7.92; N, 5.41. Found: C, 61.71; H, 7.86; N, 5.35.

50 Anal. calcd. for $C_{37}H_{55}N_3O_6S_3$: C, 60.54; H, 7.55; N, 5.72. Found: C, 60.26; H, 7.61; N, 5.63.

51 Anal. calcd. for $C_{39}H_{59}N_3O_6S_3$: C, 61.47; H, 7.80; N, 5.51. Found: C, 61.27; H, 7.89; N, 5.44.

52 Anal. calcd. for $C_{41}H_{63}N_3O_6S_3$: C, 62.32; H, 8.04; N, 5.32. Found: C, 62.19; H, 8.00; N, 5.33.

54 Anal. calcd. for $C_{42}H_{65}N_3O_6S_3H_2O$: C, 61.35; H, 8.21; N, 5.11. Found: C, 61.34; H, 8.07; N, 5.05.

55 Anal. calcd. for $C_{39}H_{59}N_3O_6S_3$: C, 61.47; H, 7.80; N, 5.51. Found: C, 61.54; H, 7.79; N, 5.51.

56 Anal. calcd. for $C_{41}H_{63}N_3O_6S_3$: C, 62.32; H, 8.04; N, 5.32; S, 12.17. Found: C, 62.40; H, 8.08; N, 5.25; S, 12.07.

57 Anal. calcd. for $C_{43}H_{67}N_3O_6S_3$: C, 63.12; H, 8.25; N, 5.14. Found: C, 63.21; H, 8.23; N, 5.04.

63 Anal. calcd. for $C_{24}H_{36}N_2O_4S_2$: C, 59.97; H, 7.55; N, 5.83. Found: C, 59.83; H, 7.56; N, 5.76.

64 Anal. calcd. for $C_{40}H_{61}N_3O_6S_3$: C, 61.90; H, 7.92; N, 5.41. Found: C, 62.03; H, 7.97; N, 5.33.

65 Anal. calcd. for $C_{12}H_{19}NO_2S$: C, 59.72; H, 7.93; N, 5.80. Found: C, 59.69; H, 7.88; N, 5.80.

66 Anal. calcd. for $C_{15}H_{24}BrNO_2S$: C, 49.72; H, 6.68; N, 3.87. Found C, 49.97; H, 6.76; N, 3.83.

67 Anal. calcd. for $C16H_{26}BrNO_2S$: C, 51.06; H, 6.96; N, 3.72. Found: C, 51.17; H, 6.95; N, 3.74.

68 Anal. calcd. for $C_{22}H_{24}N_2$: C, 83.50; H, 7.64; N, 8.85. Found C, 83.42; H, 7.67; N, 8.86.

70 Anal. calcd. for $C_{31}H_{34}N_2O_2S$: C, 74.67; H, 6.87; N, 5.62. Found: C, 74.62; H, 6.89; N, 5.54.

71 Anal. calcd. for $C_{32}H_{36}N_2O_2S$: C, 74.97; H, 7.08; N, 5.46. Found: C, 74.71; H, 7.12; N, 5.51.

72 Anal. calcd. for $C_{47}H_{59}N_3O_4S_2$: C, 71.09; H, 7.49; N, 5.29. Found C, 71.35; H, 7.53; N, 5.18.

73 Anal. calcd. for $C_{47}H_{59}N_3O_4S_2$: C, 71.09; H, 7.49; N, 5.29. Found C, 71.16; H, 7.46; N, 5.33.

74 Anal. calcd. for $C_{48}H_{61}N_3O_4S_2$: C, 71.34; H, 7.61; N, 5.20. Found C, 71.22; H, 7.64; N, 5.10.

76 Anal. calcd. for $C_{51}H_{76}N_4O_8S_4$: C, 61.17; H, 7.65; N, 5.59. Found: C, 61.21; H, 7.67; N, 5.58.

77 Anal. calcd. for $C_{16}H_{26}ClNO_2S$: C, 57.90; H, 7.90; N, 4.22. Found: C, 57.98; H, 7.82; N, 4.27.

79 Anal. calcd. for $C_{54}H_{82}N_4O_8S_4$: C, 62.16; H, 7.92; N, 5.37. Found: C, 62.30; H, 7.86; N, 5.37.

What is claimed is:

1. A polyamine which does not occur in nature having the formula:

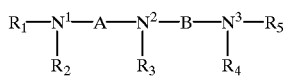

or a salt thereof with a pharmaceutically acceptable acid wherein:

$R_1$–$R_5$ may be the same or different and are alkyl, aryl, aryl alkyl, cyclo-alkyl or hydrogen; at least one of said $R_1$, and $R_2$ and at least one of said $R_4$ and $R_5$ are not hydrogen, and any of said alkyl chains may optionally be interrupted by at least one etheric oxygen atom, excluding $N^1,N^3$-diethylspermidine and $N^1,N^3$-dipropylspermidine;

$N^1,N^2$ and $N^3$ are nitrogen atoms capable of protonation at physiological pH's; and A and B may be the same or different and are bridging groups selected from the group consisting of alkylene branched alkylene, cycloalkylene, arlalkylene or unsubstituted heterocyclic bridging groups which effectively maintain the distance between the nitrogen atoms such that the polyamine:

(i) is capable of uptake by a target cell upon administration of the polyamine to a human or non-human animal; and (ii) upon uptake by said target cell, competitively binds via an electrostatic interaction between the positively charged nitrogen atoms to substantially the same biological counter-anions as the intracellular natural polyamines in the target cell, provided that where A or B is a heterocyclic bridging group, the bridging group is an unsubstituted heterocyclic group incorporating said $N^1, N^2$ or $N^3$ atom in the heterocyclic ring as an unsubstituted N atom; said polyamine, upon binding to the biological counter-anion in the cell, functions in a manner biologically different than said intracellular polyamines.

2. A polyamine according to claim 1, upon binding to said biological counter-anion in said cell, exerting an antineoplastic function.

3. The polyamine according to claim 1 having the formula:

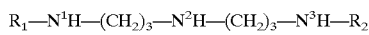

wherein: $R_1$ and $R_2$ may be the same or different and are alkyl having up to 10 carbon atoms.

4. The polyamine of claim 3 wherein $R_1=R_2=$methyl.
5. The polyamine of claim 3 wherein $R_1=R_2=$ethyl.
6. The polyamine of claim 3 wherein $R_1=R_2=$n-propyl.
7. The polyamine of claim 3 wherein $R_1=$H and $R_2=$ethyl.
8. The polyamine of claim 3 wherein $R_1=$H and $R_2=$n-propyl.

9. The polyamine according to claim 1 having the formula:

wherein: $R_1$ and $R_2$ may be the same or different and are alkyl having up to 10 carbon atoms.

10. The polyamine of claim 9 wherein $R_1=R_2=$methyl.
11. The polyamine of claim 9 wherein $R_1=R_2=$ethyl.
12. The polyamine of claim 9 wherein $R_1=R_2=$n-propyl.
13. The polyamine of claim 9 wherein $R_1=$ethyl and $R_2=$H.
14. The polyamine of claim 9 wherein $R_1=$H and $R_2=$ethyl.
15. The polyamine of claim 9 wherein $R_1=$n-propyl and $R_2=$H.
16. The polyamine of claim wherein $R_1=$H and $R_2=$n-propyl.

17. The polyamine according to claim 1 having the formula:

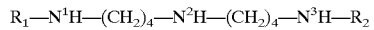

wherein: $R_1$ and $R_2$ may be the same or different and are alkyl having up to 10 carbon atoms.

18. The polyamine of claim 17 wherein $R_1=R_2=$methyl.
19. The polyamine of claim 17 wherein $R_1=R_2=$ethyl.
20. The polyamine of claim 17 wherein $R_1=R_2=$n-propyl.
21. The polyamine of claim 17 wherein $R_1=$H and $R_2=$ethyl.
22. The polyamine of claim 17 wherein $R_1=$H and $R_2=$n-propyl.

23. The polyamine according to claim 1 having the formula:

wherein: $R_1$ and $R_2$ may be the same or different and are alkyl having up to 10 carbon atoms.

24. The polyamine of claim 23 wherein $R_1=R_2=$methyl.
25. The polyamine of claim 23 wherein $R_1=R_2=$ethyl.
26. The polyamine of claim 23 wherein $R_1=R_2=$n-propyl.

27. The polyamine according to claim 1 having the formula:

wherein: $R_1$ and $R_2$ may be the same or different and are alkyl having up to 10 carbon atoms.

28. The polyamine of claim 23 wherein $R_1=R_2=$methyl.
29. The polyamine of claim 23 wherein $R_1=R_2=$ethyl.
30. The polyamine of claim 23 wherein $R_1=R_2=$n-propyl.

31. A pharmaceutical composition in unit dosage form comprising a pharmaceutically acceptable carrier and a pharmaceutically effective amount of a polyamine of claim 1 or a salt thereof with a pharmaceutically acceptable acid.

32. The pharmaceutical composition of claim 31 comprising an amount of said polyamine or salt pharmaceutically effective to treat a human or non-human patient afflicted with tumor cells sensitive to said polyamine or salt thereof.

33. A method of treating a human or non-human patient in need thereof comprising administering thereto a pharmaceutically effective amount of a polyamine of claim 1 or a salt thereof with a pharmaceutically acceptable acid.

34. The method according to claim 33 comprising administering to said patient afflicted with tumor cells sensitive to said polyamine or salt thereof an amount of said polyamine or salt thereof pharmaceutically effective to inhibit the growth of said tumor cells.

35. A polyamine according to claim 1, wherein at least one of A and B is an unsubstituted heterocyclic bridging group.

* * * * *

UNITED STATES PATENT AND TRADEMARK OFFICE
CERTIFICATE OF CORRECTION

PATENT NO. : 6,235,794 B1
DATED : May 22, 2001
INVENTOR(S) : Raymond J. Bergeron, Jr.

It is certified that error appears in the above-identified patent and that said Letters Patent is hereby corrected as shown below:

Column 44,
Line 67, the comma -- , -- was omitted after "alkylene".

Column 45,
Line 51, claim number -- 9 -- was omitted after "claim".

Signed and Sealed this

Twenty-seventh Day of November, 2001

Attest:

NICHOLAS P. GODICI
*Attesting Officer*    *Acting Director of the United States Patent and Trademark Office*